United States Patent [19]

Pappas et al.

[11] Patent Number: 4,470,158
[45] Date of Patent: Sep. 11, 1984

[54] JOINT ENDOPROSTHESIS

[75] Inventors: Michael J. Pappas; Frederick F. Buechel, both of Irvington, N.J.

[73] Assignee: Biomedical Engineering Corp., South Orange, N.J.

[21] Appl. No.: 199,928

[22] PCT Filed: Mar. 9, 1979

[86] PCT No.: PCT/US79/00147
§ 371 Date: Nov. 13, 1979
§ 102(e) Date: Nov. 13, 1979

[87] PCT Pub. No.: WO79/00739
PCT Pub. Date: Oct. 4, 1979

Related U.S. Application Data

[63] Continuation of Ser. No. 885,273, Mar. 10, 1978, abandoned.

[51] Int. Cl.³ .............................................. A61F 1/24
[52] U.S. Cl. ......................................... 3/1.911; 3/1.91; 128/92 C
[58] Field of Search ................................... 3/1.9–1.913; 128/92 C

[56] References Cited

U.S. PATENT DOCUMENTS

| | | | |
|---|---|---|---|
| 3,816,855 | 6/1974 | Saleh | 3/1.911 |
| 3,878,566 | 4/1975 | Bechtol | 3/1.91 |
| 3,964,106 | 6/1976 | Hutter, Jr. et al. | 3/1.911 |
| 4,016,606 | 4/1977 | Murray et al. | 3/1.911 |
| 4,041,550 | 8/1977 | Frazier | 3/1.91 |
| 4,081,866 | 4/1978 | Upshaw et al. | 3/1.911 |
| 4,085,466 | 4/1978 | Goodfellow et al. | 3/1.911 X |
| 4,094,017 | 6/1978 | Matthews et al. | 3/1.911 |
| 4,216,549 | 8/1980 | Hillberry et al. | 3/1.911 |
| 4,219,893 | 9/1980 | Noiles | 3/1.911 |

FOREIGN PATENT DOCUMENTS

| | | | |
|---|---|---|---|
| 2545821 | 4/1976 | Fed. Rep. of Germany | 3/1.911 |
| 2550704 | 5/1976 | Fed. Rep. of Germany | 3/1.911 |
| 2220235 | 10/1974 | France | 3/1.91 |

Primary Examiner—Ronald L. Frinks
Attorney, Agent, or Firm—R. Gale Rhodes, Jr.

[57] ABSTRACT

Joint endoprosthesis for the total replacement of degenerate joints such as the ankle, knee, elbow, wrist and finger. When embodied as an ankle endoprosthesis (10), the device comprises a tibial component (11) for being secured to the tibia and which provides a first bearing surface (21a); a talar component (13) for being secured to the talus anhd which provides a second bearing surface (34) which is at least a segment of a surface of revolution about a first axis; and a tibial insert (12) intermediate the tibial and talar components (11 and 13) which provides a third bearing surface (26a) which provides area contact with the first bearing surface (21a) and which is engageable therewith to permit relative rotation between the tibial component (11) with respect to the tibial insert (12) and the talar component (13) about a second axis which is not parallel to the first axis and is substantially parallel to the shaft of the tibia and which relative rotation provides one of only two degrees of freedom of rotational movement of said tibia with respect to said talus, and wherein the tibial insert (12) is further provided with a fourth bearing surface (29) in area contact with the second bearing surface (34) which is no more than one-half a complete surface of revolution and for area contact sliding engagement therewith to permit relative rotational movement of the tibial component (11) and tibial insert (12) with respect to the talar component (13) about the first axis which relative rotation thereby provides the second of only two degrees of freedom of rotational movement of said tibia with respect to said talus so long as these bearing surfaces are kept in area contact but allowing a third rotational motion by partial separation of these surfaces.

18 Claims, 66 Drawing Figures

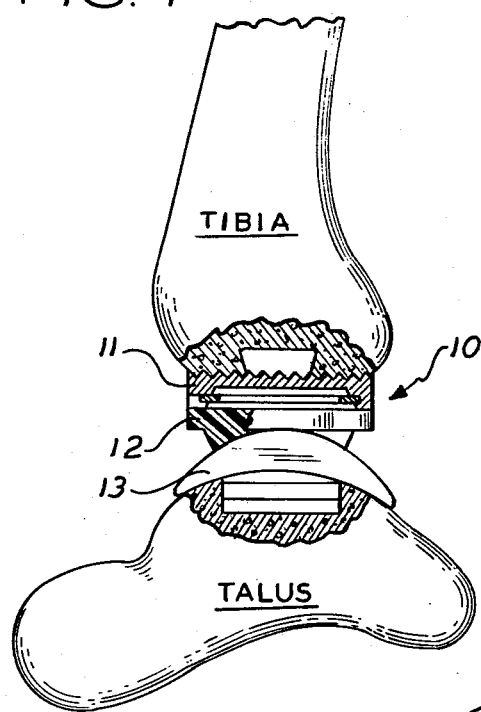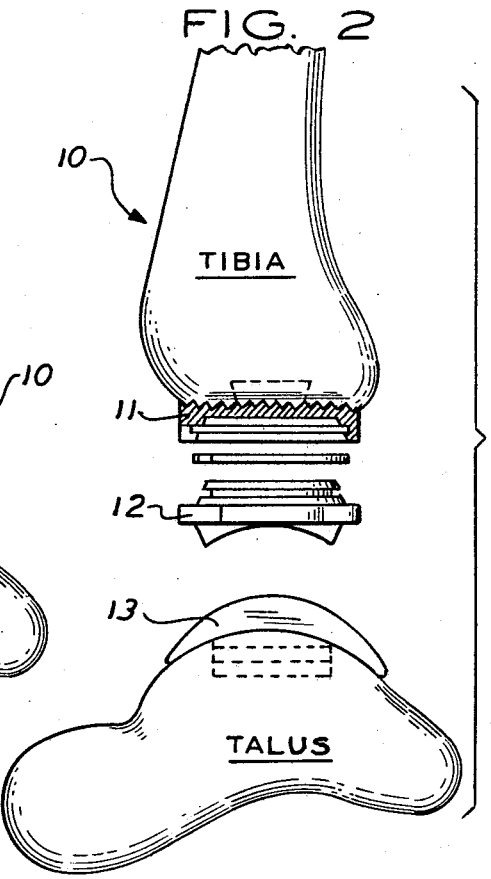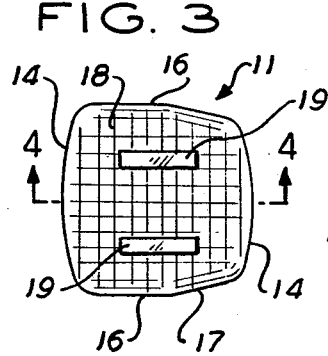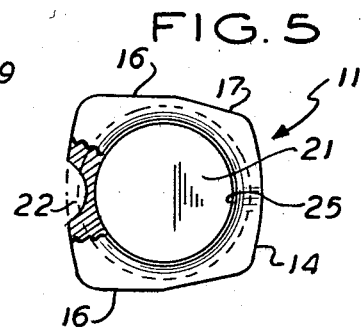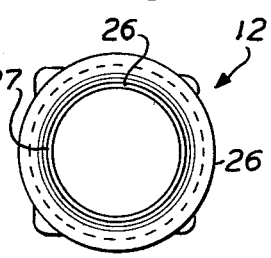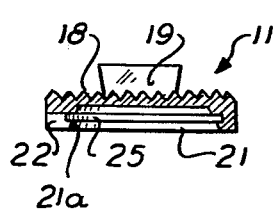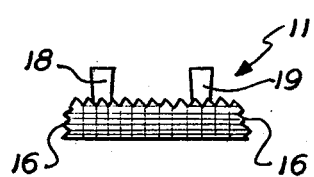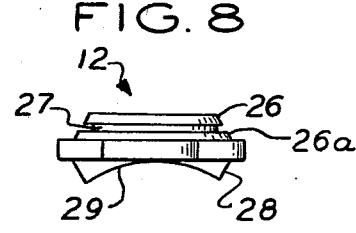

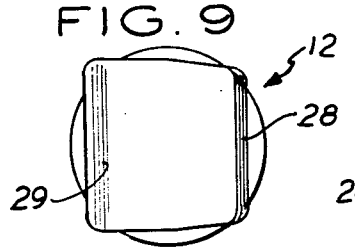
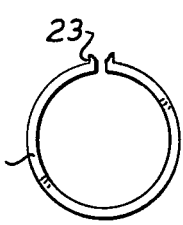
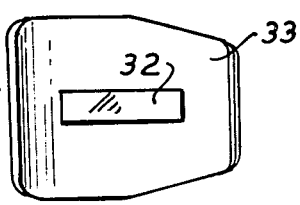
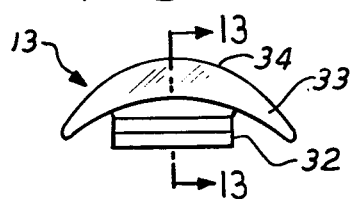
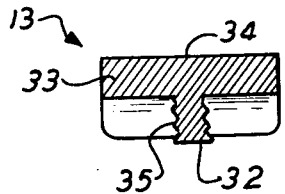
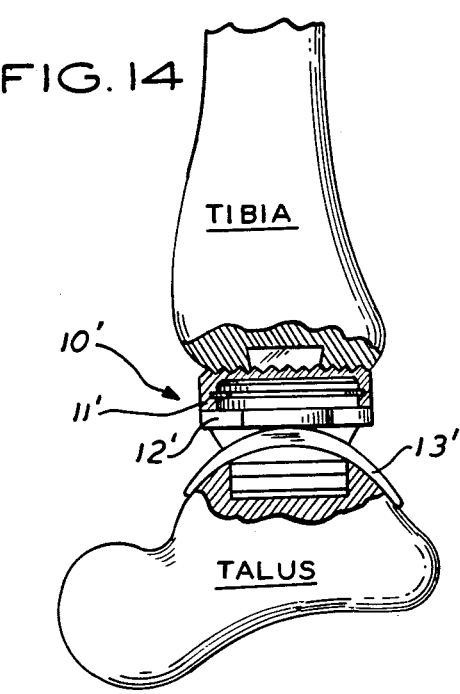
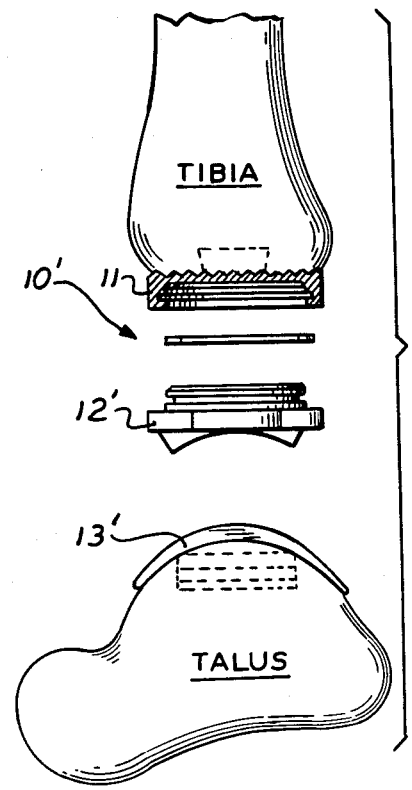

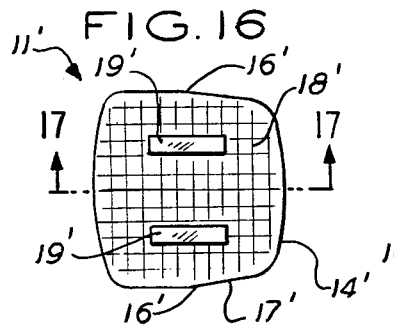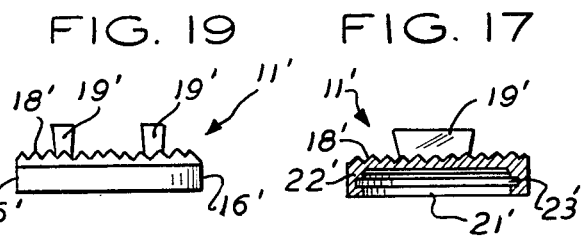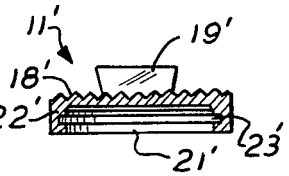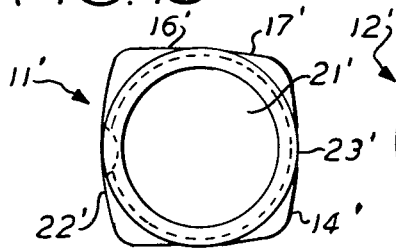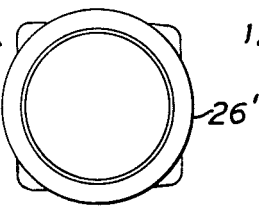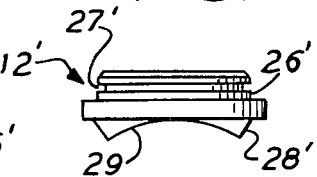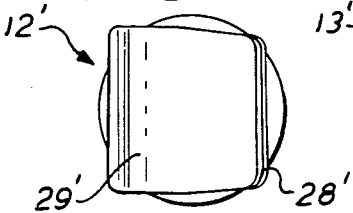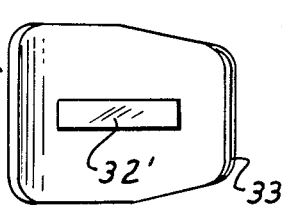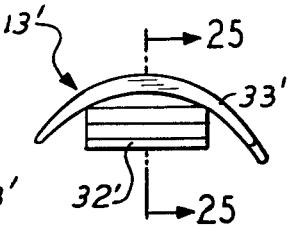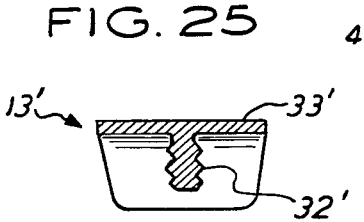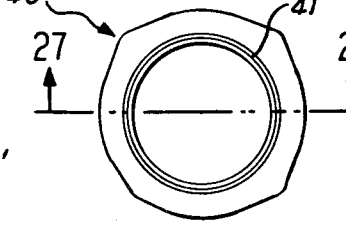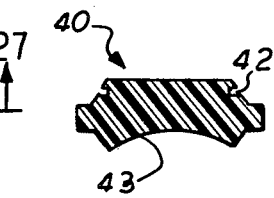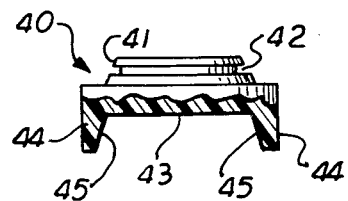

FIG. 34
FIG. 35
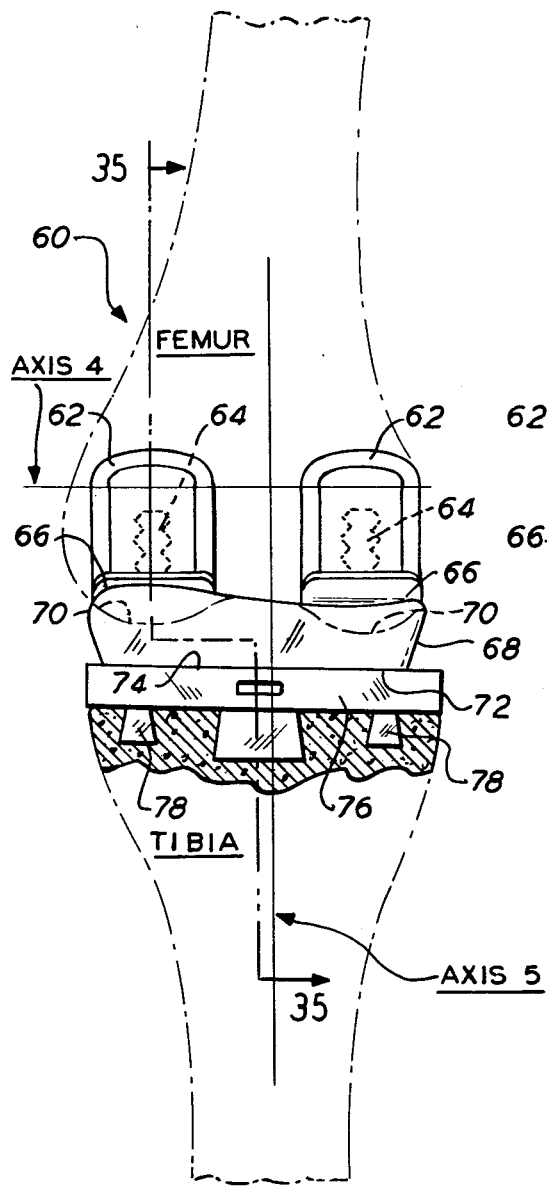
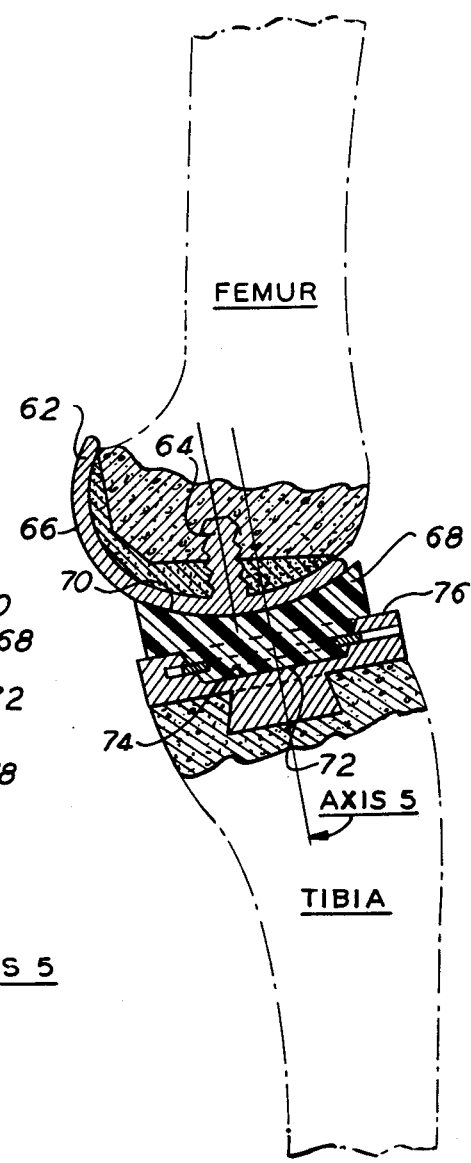

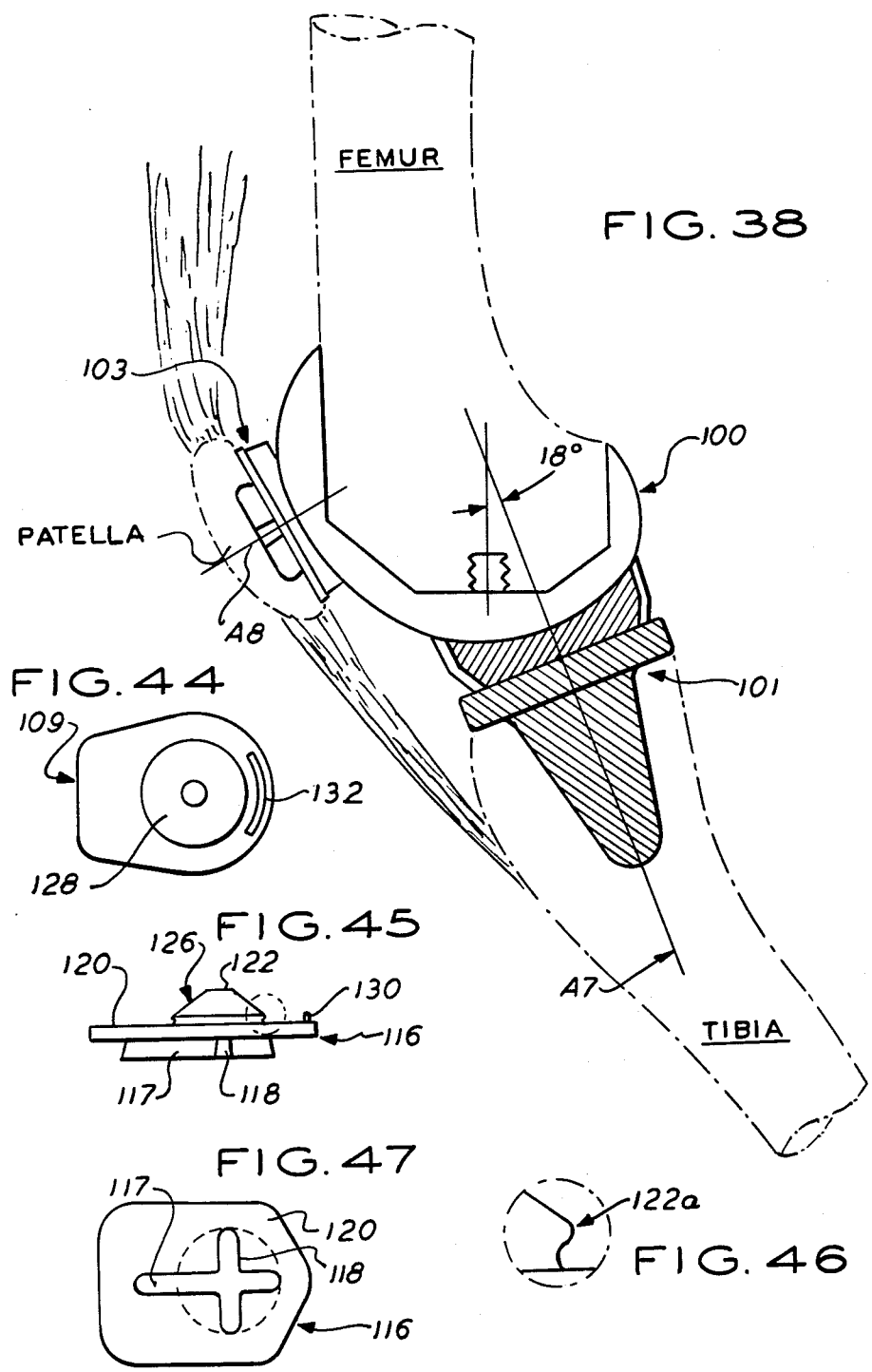

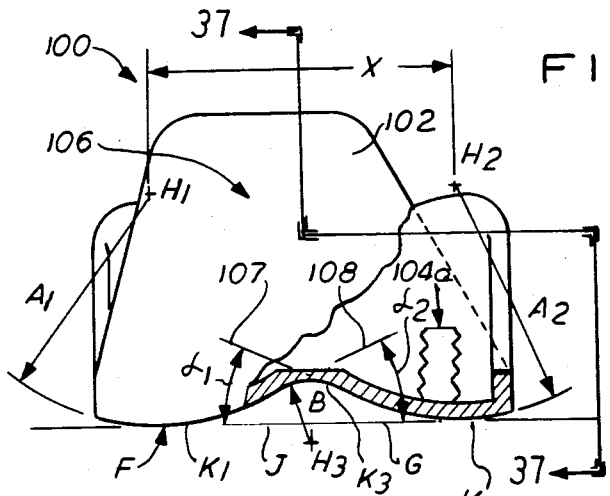
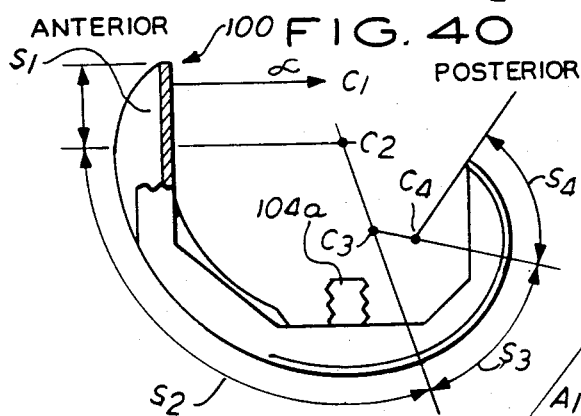
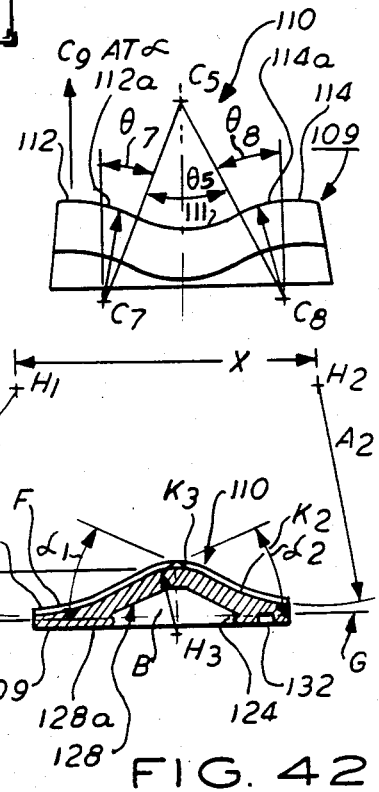
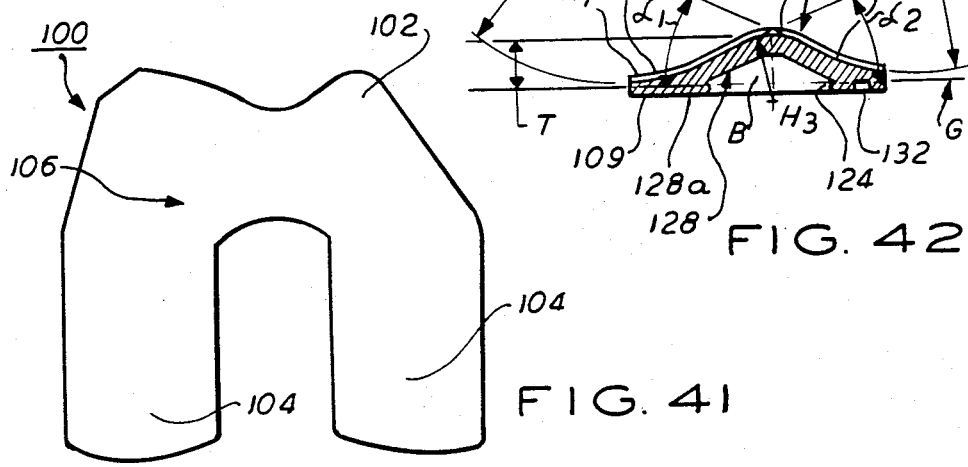
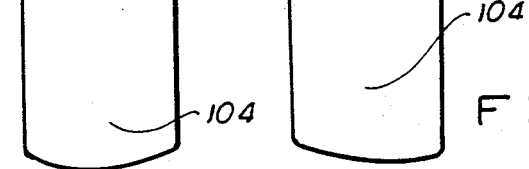

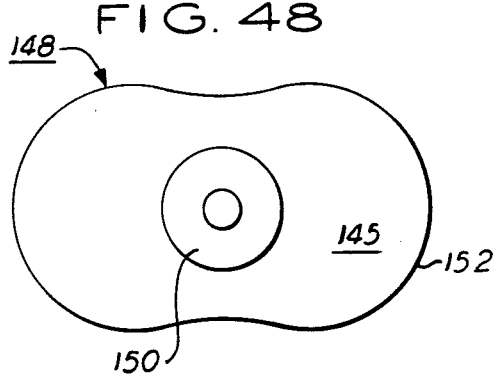
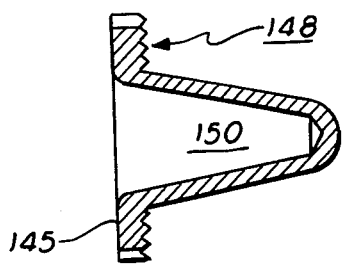
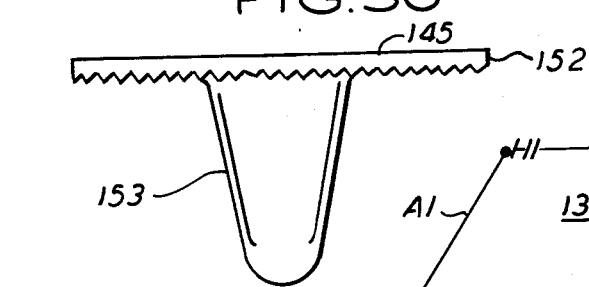
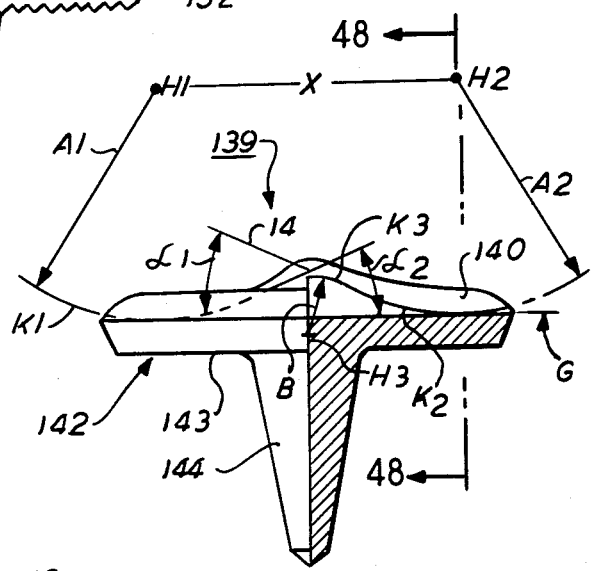
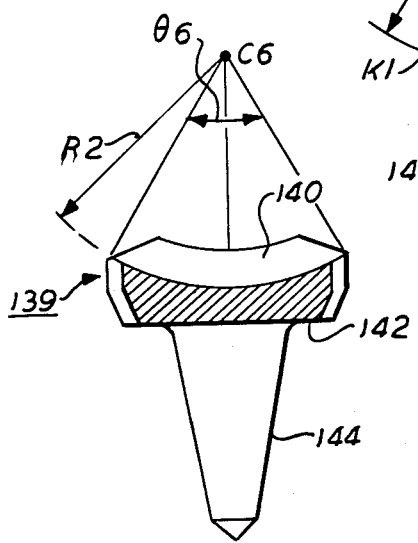
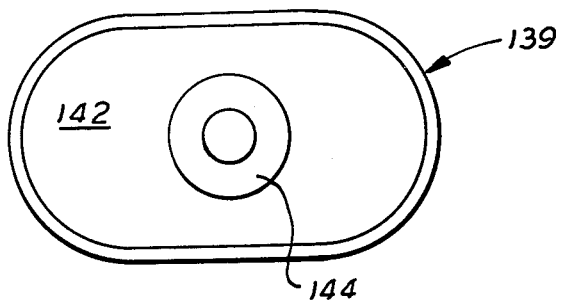

$F_Q$  
R  
$F_Q'$  
DEEP FLEXION

FEMUR  
PATELLA  
TIBIA

FEMORAL ANTERIOR ARTICULAR CARTILIGE FOR PATELLA-FEMORAL ARTICULATION

FEMORAL POSTERIOR ARTICULAR CARTILIGE FOR TIBIO-FEMORAL ARTICULATION

THIS END TENDS TO LIFT  
R  
COMPRESSION LOAD IN FULL EXTENTION  
THIS END IS DEPRESSED

OVERLAP AVAILABLE WITH CONGRUENT DESIGN

INCONGRUENT OVERLAP

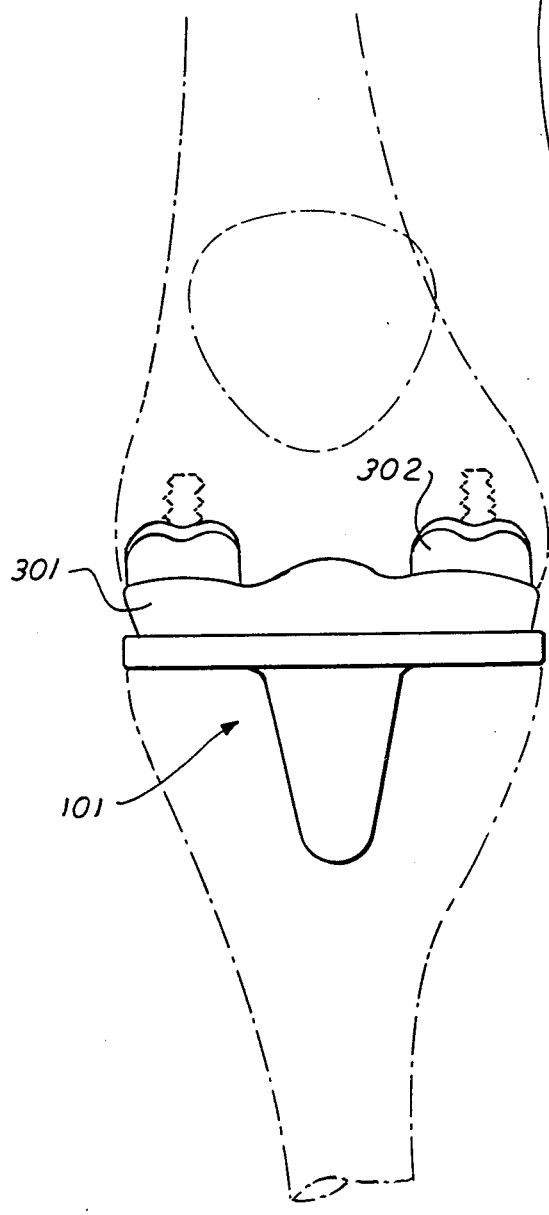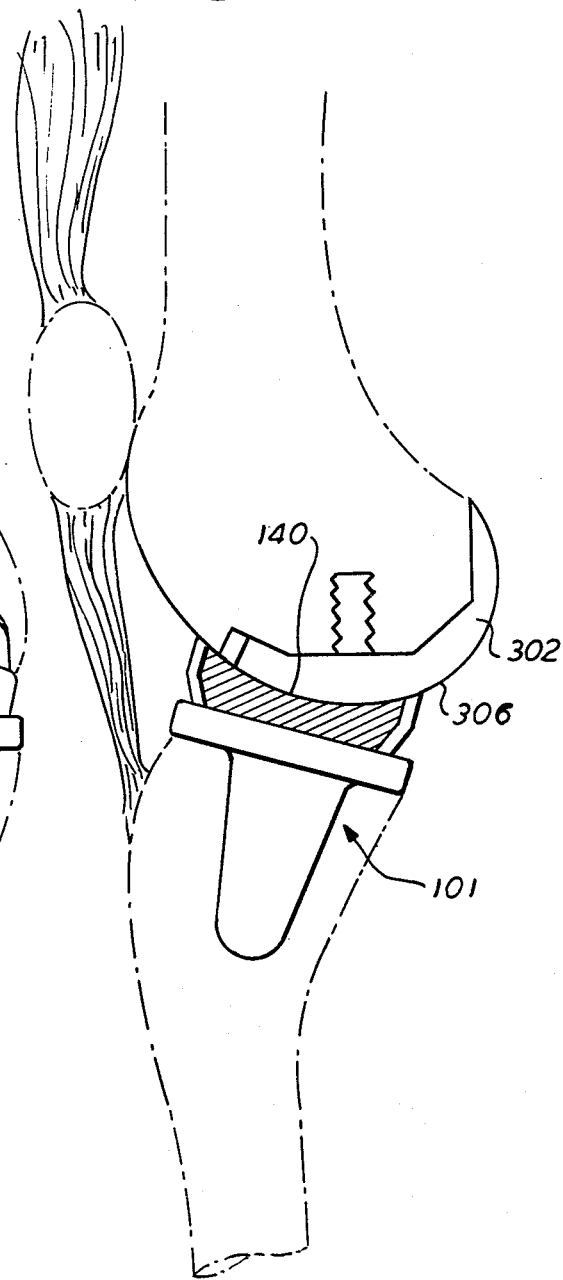
FIG. 60
FIG. 61

JOINT ENDOPROSTHESIS

CROSS REFERENCE TO OTHER APPLICATIONS

This application is the United States National application corresponding to International Application No. PCT/US 79/00147 filed Mar. 9, 1979 the benefit of which filing date is claimed. This application is also a continuation in part application of parent application Ser. No. 885,273 filed Mar. 10, 1978, now abandoned, the benefit of which filing date is claimed.

TECHNICAL FIELD

Broadly speaking, this invention relates to joint endoprotheses and more specifically to a joint endoprosthesis with area contact bearing engagement and only two degrees of freedom of rotational movement between a first bone and a second bone while the bearing surfaces are kept in area contact engagement under the action of the joint.

BACKGROUND ART

For the sake of brevity and convenience, the discussion of the prior art here will be generally limited to the ankle, and prior art ankle prostheses with later discussion of the knee; accordingly:

As is known to those skilled in the art, until quite recently, fusion was the primary mode of treatment for the most disabling conditions of the ankle joint. The reason for this was that fusion of the ankle produces much less disfigurement and loss of function than does fusion of any other major load-bearing joint. Thus, ankle fusion, even with its attendant loss of function, remains a therapeutically acceptable procedure. Nevertheless, fusion, by its very nature, should be considered redical surgery—the last possible alternative in joint reconstruction. If effective prosthetic surfaces can restore normal ankle function, then such an alternative is certainly more desirable than fusion.

The article by Pappas, Buechel and DePalma entitled "Cylindrical Total Ankle Joint Replacement" which appeared in *Clinical Orthopaedics and Related Research*, No. 118, July-August 1976, pp. 82-92, surveys the various ankle prostheses which have been developed to date. All such prostheses are metal-to-plastic articular surface replacement types which essentially rely on ligamentous control for stability. The fundamental differences in the various designs lie in the nature of the articulating surfaces. Two basic types are found: those with theoretical line or point contact articulating surfaces and those with area contact articulating surfaces.

The incongruent surface types all permit the normally observed axial rotation in addition to permitting flexion-extension. However, incongruent surface prostheses suffer from two basic defects: (1) relatively poor wear and poor deformation resistance due to high local stress resulting from incongruent surface contact, and (2) relatively poor inherent stability. High local stresses and pressures resulting from normal walking loads, even with a relatively small amount of incongruity, result in permanent deformation of the ultra-high molecular weight polyethylene (UHMWPE) used in all known current ankle prostheses, as well as a relatively high wear rate.

In addition, since the human ankle joint possesses essentially congruent surfaces, one cannot expect an incongruent replacement joint to approximate normal motion since the kinematic properties of congruent and incongruent surfaces are so different.

Prostheses utilizing congruent or area contact surfaces, on the other hand, have good pressure distribution and, thus, offer superior wear and surface deformation resistance when compared to incongruent types. Further, they provide nearly normal stability because, under compressive load, the surfaces are forced into conformity and therefore motion to a large extent is defined by the surface geometry, thus providing predictable motion characteristics. Four basic variations of the area contact surface prosthesis are known. These are (1) spherical (e.g. ball and socket); (2) spheroidal (e.g. barrel-shaped); (3) cylindrical; and (4) conical.

The spherical prosthesis allows three independent axes of rotation but the joint surface geometry dictated by such a design tends to limit the flexion-extension range. Further, the spherical type ankle prosthesis is also less resistant to inversion-eversion injuries caused by substantially greater than normal loading of the ligaments and also is unstable since it allows an inversion-eversion motion between the tibia and talus that is not normally present. This lack of stability has been observed clinically.

The spheroidal type of prosthesis provides two independent rotations, plantar and dorsiflexion and inversion-eversion but fails to provide axial rotation. Thus, spheriodal prostheses are undesirable since axial rotation is necessary for normal function and since the device is also unstable in the inversion-eversion mode.

The conical type of prosthesis employs dual cones with a single horizontal axis. This design has an ample range of motion but it obtains this motion by the use of a substantially higher than normal rotation axis. Furthermore, this particular prosthesis requires significantly greater resection of bone than some other designs.

The cylindrical prosthesis, described in the above referred to article by Pappas et al. overcomes many of the noted deficiencies of the other congruent surface devices. Briefly, the device described by Pappas et al. employs a cylindrical surface with a horizontal axis located at the center of curvature of the lateral border of the talar dome. The cylindrical surface uses a UHMWPE talar component and a mortised cobalt-chromium alloy tibial component both of which are stabilized with methyl-methacrylate bone-cement and dual fixation fins.

As previously mentioned, the advantages of the cylindrical or conical configurations are internal stability, approximating that of the normal ankle, and good congruent contact producing low stress and wear. Unfortunately, a conventional cylindrical or conical joint does not provide for the axial rotation which is normally observed in ankle motion.

Strictly speaking, this rotation is not needed to provide a normal gait since it is not present at all in about 3 to 5% of normal individuals. However, in most individuals, the loading pattern and walk are such that axial rotation tends to be induced and if it is not provided for in the prosthesis, stress is imparted to the fixation means and on those components of the prosthesis which resist axial rotation, thereby introducing the possibility of loosening of the prosthesis or deformation or wear of the prosthesis.

More specifically, deformation and wear associated with the need for axial rotation have been found in a prosthesis that was removed from a patient after loosening of the prosthesis was encountered. It is believed that a major factor in this loosening was the failure of this early prosthesis to provide any degree of axial rotation.

Furthermore, it is known when heavy loads are impressed on a relatively thin plastic prosthesis the component tends to loosen. The explanation for this is that since a relatively weak and brittle substance is used to cement the plastic component to bone, when the plastic is deformed under load it easily bends transmitting this bending to the cementing material which is then subject to cracking, producing a loosening of the prosthesis. On the other hand, when this same brittle cement is used to fixture metal to bone, the metal is so rigid that bending is inhibited and therefore the bending stresses which tend to produce cracking on the cement are reduced to a level where they are no longer of concern. Thus the metal protects the cement.

Thus it is important that a prosthesis for a typical condylar type joint possess axial rotation and be fixtured to bone by use of a strong rigid material such as metal. This statement is supported by extensive clinical studies involving hundreds of patients with knee replacements which show that it is the plastic component, that most frequently fails by loosening or excessive deformation and that although these failures commonly occur in incongruent designs they are much more frequent in congruent designs which restrain axial rotation.

In view of the above, it is clearly desirable to affix a metal rather than plastic prosthesis to bone. Because metal-to-metal contact surfaces do not wear well and since the wear products cause adverse tissue reaction it is necessary to interpose a non-metallic bearing into the prosthesis.

The instant invention is based on the discovery that since it appears necessary in any event to interpose a third part in the prosthesis, if this part is implemented as a non-metallic insert, designed in such a manner that it provides the desired axial rotation, the previously discussed objectives will be attained. Futhermore, axial rotation of the prosthesis also compensates for surgical malalignment. That is, the components of the prosthesis inserted into the ankle can be slightly rotated. The ability of the insert to rotate axially accommodates for this rotational error.

SUMMARY OF THE INVENTION

In a preferred embodiment of the invention, and when embodied as an ankle prosthesis, the device comprises a tibial component for being secured to the tibia and providing a first bearing surface; a talar component for being secured to the talus and providing a second bearing surface which is at least a segment of a surface of revolution about a first axis, and a tibial insert intermediate the tibial and talar components and provided with a third bearing surface which provides area contact with the first bearing surface and engageable therewith to permit relative rotation of the tibial component with respect to the tibial insert and talar component about a second axis which is not parallel to the first axis and is substantially parallel to the shaft of the tibia and which provides one of only two degrees of freedom of rotational movement of said tibia with respect to said talus, and wherein the tibial insert is further provided with a fourth bearing surface in area contact with the second bearing surface which is no more than one half a complete surface of revolution and for area contact sliding engagement therewith to permit relative rotational movement of the tibial component and tibial insert with respect to the talar component about the first axis and which provides the second of only two degrees of freedom of rotational movement of the tibia with respect to the talus so long as these bearing surfaces are kept in area contact but allowing a third rotational motion by partial separation of these surfaces.

The invention, and mode of operation will be more fully comprehended from the following detailed description, when taken with the appended drawings in which:

BRIEF DESCRIPTION OF THE DRAWINGS

FIG. 1 is a partial cross-sectional view of an ankle joint prosthesis embodying the present invention;

FIG. 2 is an "exploded" version of FIG. 1 showing the three major components of the prosthesis in greater detail;

FIGS. 3–5 are respectively the top, cross-sectional and bottom views of the tibial component of the prosthesis shown in FIGS. 1–2;

FIGS. 7–9 are respectively the top, side and bottom views of the tibial insert component of the prosthesis shown in FIGS. 1 and 2;

FIG. 10 shows the front and side of the snap ring used to unite the components shown in FIGS. 3–5 and 7–9;

FIGS. 11–13 are respectively the bottom, side and cross-sectional views of the talar component of the prosthesis shown in FIGS. 1 and 2;

FIGS. 14 and 15 are respectively the normal and "exploded" cross-sectional views of a second illustrative embodiment of the invention;

FIGS. 16–18 are respectively the top, cross-sectional and bottom views of the tibial component of the prosthesis shown in FIGS. 14 and 15;

FIG. 9 is a side view of the tibial component shown in FIGS. 16–18;

FIGS. 20–22 are respectively the top, side and bottom views of the tibial insert component of the prosthesis shown in FIGS. 14 and 15;

FIGS. 23–25 are respectively the bottom, side and cross-sectional views of the talar component of the prosthesis shown in FIGS. 14 and 15;

FIGS. 26–28 are respectively the top, cross-sectional and side views of an alternate embodiment of the tibial insert component shown in FIGS. 7–9;

FIG. 34 is a front or anterior view of a knee joint prosthesis embodying the present invention; and FIG. 35 is a cross-sectional view taken along the line 35—35 of FIG. 34;

FIGS. 36, 37 and 38 are partial cross-sectional views showing an alternate embodiment of the present invention embodied as a tricompartmental knee prosthesis;

FIGS. 39, 40 and 41, are, respectively, top, side and front views of the femoral component of the alternate embodiment of the present invention embodied as a knee prosthesis;

FIGS. 42, 43, and 44 are, respectively, cross-sectional top, side and front views of the intermediate patella bearing component of the alternate embodiment of the present invention embodied as a knee prosthesis;

FIGS. 45, 46 and 47 are, respectively, top, partially enlarged and front views of the patella fixturing component of the alternate embodiment of the present invention embodied as a knee prosthesis;

FIGS. 48, 49 and 50 are, respectively, top, cross-sectional side and front views of the tibial fixturing component of the alternate embodiment of the present invention embodied as a knee prosthesis;

FIGS. 51, 52 and 53 are, respectively, front, partial cross-sectional side and front views of the tibial intermediate component of the alternate embodiment of the present invention embodied as a knee prosthesis;

FIGS. 58 and 59 and FIGS. 60 and 61 are, respectively, back, side views of the femoral component embodying the present invention embodied as a bicompartmental knee prosthesis;

DETAILED DESCRIPTION OF THE INVENTION

Figure 29:
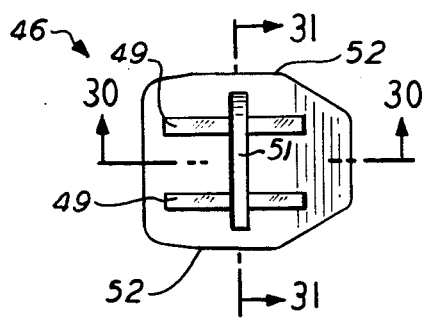
FIGS. 29–31 are respectively the bottom, cross-sectional and cross-sectional side views of a talar dome replacement prosthesis for use with the tibial insert component shown in FIGS. 26–28.

FIG. 1 depicts an ankle prosthesis embodying the present invention in its intended environment, the human ankle. As will be shown later, however, the present invention is not so limited and with appropriate changes in dimension and configuration it may be used with equal facility in any other dysfunctional human joint of similar construction as noted above.

As shown in more detail in the "exploded" view of FIG. 2, endoprosthesis 10 comprises a tibial component 11, a bearing insert 12 and a talar component 13.

While the method by which prosthesis 10 is implanted forms no part of the instant invention and, indeed, may vary from surgeon to surgeon, it is instructive to briefly review the normal operative procedure.

First, the surgeon osteotomizes the distal tibia to receive tibial component 11, but component 11 is not installed at this time. Next, the talus is slotted to receive talar component 13 which, after the surgeon is satisfied with the slot cut into the talus, is then cemented into place. Then, tibial component 11 is cemented into place and finally tibial insert 12 is snapped into tibial component 11 to provide the desired axial rotation and bearing surface. Advantageously, both the tibial and talar components are fabricated from a Co-Cr-Mo alloy while the bearing insert is fabricated from a non-metallic material such as ultra-high molecular weight polyethylene (UHMWPE). Of course, other materials may be substituted provided that they are biologically compatible and satisfy the stress and wear requirements of the prosthesis. For example, ceramics and carbon-fiber filled UHMWPE have been considered for the bearing insert. Stainless steel or any of the known titanium, nickel, or titanium-vanadium aluminum alloys could similarly be used for the tibial and talar components. Ceramics could also be used to advantage for these parts.

FIGS. 3-6 depict tibial component 11 in greater detail. FIGS. 3-5 are respectively the top, cross-sectional and bottom views of the component while FIG. 6 is an alternate cross-sectional view of the component. Referring now to FIG. 3, it will be seen that tibial component 11 has a generally rectangular configuration with one pair of rounded edges 14—14 and one pair of straight edges 16—16, the latter having a slight inward bevel 17 at one end. In the illustrative embodiment, the bevel makes an angle of about 12° to the straight edges. The upper portion 18 of component 11 is grooved in two orthogonal directions to create a serrated surface which serves to provide increased shear resistance. The serrated surface supports a pair of upwardly extending fins 19 which are tapered inwardly along all four sides to lock the cement to the fins. The fins 19 have a relatively low profile so that only a minimal resection of the distal tibia is necessary. The low fin profile also greatly facilitates the insertion of the prosthesis by the surgeon.

The overall shape of tibial component 11 closely approximates the cross-section of the tibia into which it is to be fitted. This maximizes the prosthesis-to-bone contact area which is important because a maximum contact tends to minimize tipping effects resulting from eccentric loads which tend to produce tensile loading which may pull the cement away from the bone causing the component to loosen and preventing bone growth adjacent the cement. This arrangement also minimizes compressive stress on the bone. As is well known, the closer that bone stress approaches that found in the average, healthy subject, the healthier the bone will be because excessive bone stress can cause necrosis of the bone. The tibial component shown in FIGS. 3-6 maximizes the area over which the load is applied by making the component as large as possible given the limitations of the joint space which is available. As seen best in FIG. 6, note also that edges 16 are tapered inwardly which minimizes bone resection and the serrations on these surfaces help resist tension loads resulting from possible eccentric loads. As shown in FIGS. 4 and 5, tibial component 11 includes a conical recess 21 with an axis substantially parallel to the tibial shaft which receives the non-metallic bearing insert 12. The interior of recess 21 is accurately machined and highly polished to provide a bearing surface 21a. Thus, when insert 12 is positioned within the recess, the low-friction conical bearing surface 21a permits the desired axial rotation of the ankle. Component 11 is further provided with an aperture 22 through which the ears 23 of a snap-ring 24 (FIG. 10) may pass. Recess 21 is further provided with a groove 25 which is slightly larger in diameter than recess 21. Groove 25 retains snap-ring 24 when non-metallic insert 12 is positioned within component 11.

FIGS. 7-9 are respectively the top, side and bottom views of non-metalllic intermediate bearing component or tibial insert 12. As shown, insert 12 is provided with an upwardly extending portion 26 having an upper bearing surface 26a which is congruent with bearing surface 21a of the tibial component 11 and which is for congruent rotational engagement therewith in the conical recess 21 of component 11. Upwardly extending portion 26 includes a groove 27 which aligns with groove 25 in tibial component 11 when insert 12 is mated with the component. The extreme upper edge of portion 26 of the cone spreads snap-ring 23 apart when tibial insert 12 is first positioned in recess 21. As shown in FIGS. 8 and 9, tibial insert 12 has a downwardly extending portion 28 having a cylindrically concave bearing surface 29 which is less than one half a complete surface of revolution and which is designed for area contact sliding engagement with a similarly cylindrical convex bearing surface 34 of equal, or substantially equal, radius on talar component 13 (FIG. 12). As will be noted from FIG. 9, the plan view of concave surface 29 approximates the dimension and shape of surface 18 in tibial component 11, but is slightly smaller to accommodate axial rotation.

FIGS. 11, 12 and 13 are respectively the bottom, side and cross-sectional views of talar component 13. As shown, talar component 13 comprises an upper portion 33 having an upper convex bearing surface 34 which is less than one half a complete surface of revolution and being provided with a centrally located, serrated, fixation fin 32 extending downwardly therefrom. Essentially, the upper portion 33 of component 13 comprises a segment of a cylinder. As previously discussed, the cylindrical, convex shape of bearing surface 34 is in area contact with the cylindrical, concave surface 29 of tibial insert 12 which, thus, permits low-friction, area contact, sliding relative rotational motion therebetween. This motion is constrained by the cylindrical nature of the bearing surface 34 to rotary motion about the axis of the cylinder of which upper portion 33 is a segment so long as these surfaces are kept in area contact. These surfaces may however be partially uncoupled to provide rotation about an anterior-posterior axis.

Referring momentarily to FIG. 8, it will be noted that in the illustrative embodiment, concave surface 29 has a radius of about 0.85 inches and subtends an angle of about 64°. In like fashion, in the illustrative embodiment convex surface 34 also has a radius of about 0.85 inches and subtends an angle of about 128°. Thus, when pressed into engagement for congruent, sliding rotary motion, the prosthesis 10 permits a plantar-dorsiflexion range of up to 64° without loss of area contact between surfaces 29 and 34 although in practice the angle subtended by surface 34 could range from 100° to 140° and the angle subtended by surface 29 could range from 50° to 70°. It will be noted that the angle subtended by convex bearing surface 34 is asymmetric with respect to the vertical axis being displaced 29° in the anterior direction but only 23° in the posterior direction. This results in a plantar-dorsiflexion movement which closely approximates that found in the normal foot which allows more dorsiflexion motion.

It is often extremely difficult to determine in advance what the overall height of a prosthesis should be, especially when dealing with a degenerate distorted ankle. It is thus an important aspect of the instant invention that non-metallic tibial insert 12 is removable from component 11. By providing a variety of tibial inserts, e.g. of 2, 4, 6 . . . mm height, the surgeon can try out different tibial inserts until he finds one of the appropriate height. Of course, snap-ring 24 is not used to retain tibial insert 12 until the surgeon is completely satisfied with the trial fitting. The fact that insert 12 can be easily removed during the trial fitting means that the surgeon has excellent visibility of the implanted tibial and talar components and can, thus, check for and remove, if necessary, excess bone cement and/or correct other defects. Of course, non-metallic tibial insert 12 can also be removed after it has been locked into place by snap-ring 24 because ears 23 are accessible through aperture 22 in tibial component 11.

It should also be pointed out that replacement of tibial insert 12 may also be effected during a second operation. This may be necessary to correct for excessive and unusual wear of the non-metallic component or where the surgeon feels, in retrospect, that he initially selected a tibial insert of inappropriate dimensions.

The fact that neither the fixation to the tibia nor the fixation to the talus need be disturbed during the second operation demonstrates the significant advantage that the instant endoprosthesis possesses over prior art devices.

It will also be appreciated that the radius of the bearing surface 34 of the talar component need not be as depicted in FIG. 12. In fact, the radius may be considerably larger or smaller than shown. In the illustrated talar component shown in FIG. 12, tibial insert 13 is thickest in the center, thinner in the anterior direction and thinnest in the posterior direction.

This variation in thickness and radius of curvature is intended to accommodate talar domes of different radii and the varying conditions that are typically experienced when dealing with degenerative bone. That is to say, while the shape of the talus is fairly well defined in the normal ankle joint, it is ill-defined in the pathological or degenerate joint. Of course, the reason that the endoprosthesis is needed in the first place is because the bone, or bones associated with the joint have degenerated. For that reason, the surgeon needs a variety of shapes to insure good, congruent, contact with the bone. Some incongruity can be taken up by the cement, which is typically methyl-methacrylate, but a large degree of incongruity is undesirable because the amount of cement used should normally be held to a minimum. It is, thus, another important feature of the invention that a large number of talar components can be made available to the surgeon although only one is shown in the drawings. The fixation fin used on the talar component is somewhat longer than the fixation fins used on the tibial component because access to the talus is not problem. That is, because the talar component is generally implanted before the tibial component is inserted surgical access is excellent. Another reason that the talar fin is longer than the tibial fins is that the talus is typically degenerate and the use of a long talar fixation fin permits fixation of the talar component below the region of bone degeneracy.

In fixation of the talar component, a slot is first made in the talus and the talar component is placed on the talus with the fin protruding into the slot which was priorly filled with cement. The cement does not act as an adhesive in the normal sense of the word; rather, it acts as a casting or grouting agent. It is thus necessary to mechanically interlock the talar component and talus in order to get fixation. To this end, fin 32 has longitudinal channels 35 cut in its side to provide interlocking and tensile resistance. Anterior-posterior and medial-lateral resistance are offered by the basic shape of the component in the first instance, and by the fact that the sides of the fin 32 will impinge the bone in the second instance. As previously mentioned, surface 34 is tapered on its posterior aspect in order to extend down onto the posterior or rear aspect of the talus, thereby providing a normal anatomical range of motion. Most prior art ankle prostheses do not provide such a normal range of motion and as is known, such motion is necessary for many normal activities, such as stair climbing. Certainly, no known prior art prosthesis provides this range of motion with a radius of curvature of the upper surface which approximates the normal anatomical curvature while at the same time providing congruent contact.

FIGS. 14 and 15 depict a second embodiment of the invention which uses a cylindrical rather than a conical bearing surface. As before, prosthesis 10' comprises a tibial component 11', a non-metallic insert 12' and a talar component 13' respectively shown in greater detail in FIGS. 16-19, 20-22 and 23-25. A detailed discussion of this second embodiment is not believed to be necessary. Suffice it to say that, as shown in FIG. 17, recess 21' is cylindrical rather than conical and, as shown in FIG. 21, the upper portion 26' of insert 12' is correspondingly cylindrical. Also, in this second embodiment, edges 16' of tibial component 11' are not tapered, although there is no reason they could not be if the degree of bone resection is of concern.

One of the more common defects found in prostheses using metal-to-non metal (e.g. plastic) bearing surfaces is deformation and flow of the non-metallic component under load. This cannot occur in the instant invention for two reasons: (1) because tibial insert 12 is free to rotate in the tibial component, the ankle is free to rotate axially with respect to the tibia as it wants to do, thus the extreme loads present in the prior art prostheses simply do not occur; and (2) the fact that the upper end of tibial inserts 12 and 12' are respectively confined within conical or cylindrical recesses 21 or 21' prevents excessive deformation or flow.

The two illustrative embodiments discussed so far provide unconstrained axial rotation in relation to the tibial component and unconstrained cylindrical rotation about the talar component. This novel arrangement allows physiological axial rotation of the tibia-talar joint without causing axial torque on the cement beds. Of the two metal components, the talar onlay geometry of components 13 and 13' provides a rotation center which is compatible with the lateral or constant geometry center of the normal ankle. This provides physiological loading on the lateral, or sprain prone, ligaments of the ankle.

Since good ligamentous stability is a pre-requisite for ankle replacement, internal malleoli are not provided in the first two embodiments of the invention. This allows medial-lateral thrust loads to be physiologically resisted by the ligaments and retained bony malleoli rather than by constraints of the device itself.

In situations of talar dome loss, a metal talar dome prosthesis can be used in place of onlay components 13 and 13'. In these cases, small non-metallic malleoli may be added to cylindrical inserts 12 and 12' to maintain medial-lateral stability. These malleoli are angled to allow up to 10° of talar tilt before disengaging. Thus, normal talar tilt can occur for as long as ligamentous stability is maintained. With fracture or ligamentous rupture, the components can disengage to avoid tear out stresses on the talar component. Non-metallic inserts of differing dimensions may again be used to provide optimal component placement and ligamentous tension.

More specifically, to aid the surgeon in height adjustment intraoperatively, the non-metallic component is made in various dimensions This allows precise ligamentous loading by virtue of shimming and permits superior bone-cement-prosthesis contact, since the removed bone can be shimmed with components of the device rather than by increased amounts of methylmethacrylate cement. Non-metallic components are removable to allow replacement or readjustment intraoperatively without disturbing components priorly fixtured to the bone.

FIGS. 26-28 depict an illustrative non-metallic tibial insert 40 which is equipped with malleoli. As shown, insert 40 comprises a conical, upwardly extending portion 41 having a circumferentially extending groove 42 therearound. As was the case for the non-metallic inserts previously discussed, the lower portion of insert 40 comprises a concave bearing surface 43 which subtends, in the illustrative embodiment, an angle of about 64°. As best shown in FIG. 28, insert 40 further includes a pair of malleoli 44—44 to maintain the medial-lateral stability of the prosthesis. The outer walls of the malleoli are substantially vertical but the inner walls make an angle of about 10° to the vertical. Thus, up to 10° of talar tilt is possible without disengagement.

Figure 30:
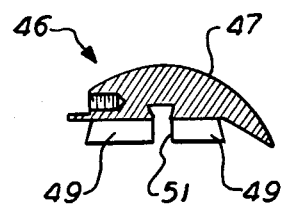
Figure 31:
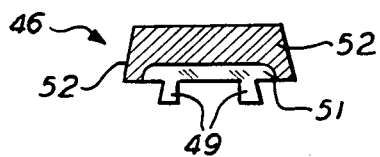
Figure 32:
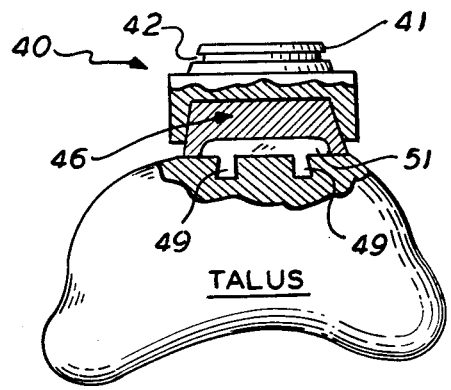
FIG. 32 is a cross-sectional view showing how the tibial insert component of FIGS. 26–28 can be mated with the talar dome replacement of FIGS. 29–31.

FIGS. 29-31 depict the talar dome component required by non-metallic tibial insert 40. As shown, talar component 46 comprises an upper, convex load-bearing surface 47 essentially similar in shape to surfaces 34 and 33' in FIGS. 12 and 24, respectively. The lower surface 48 depends a pair of fins 49—49 which are cut in half by an elongated slot 51 which extends upwardly into the body of the component. Slot 51 is intended to retain the cement used to fix component 46 to the remains of the actual talar dome. To that end, the upper portion of slot 51 expands inside the main body of the prosthesis to trap additional cement and, thus, further secure talar component 46 to the talus. The outer walls 52—52 of component 46 are tapered inwardly at an angle which matches the angle at which the inner walls 45 of malleoli 44 are tapered. Thus, as shown in FIG. 32, non-metallic tibial insert 40 mates exactly with talar component 46 providing the desired medial-lateral stability. As in the case of the previously discussed prosthesis, tibial insert 40 may be made in various thicknesses to accommodate various ankle situations.

It should be noted that all the prostheses discussed above are symmetrical about the anterior-posterior axis. This means that the same prosthesis may be used in either the left of right foot, which greatly simplifies the task of the surgeon. This symmetry is best seen in FIGS. 3, 11 and 29.

Figure 33:
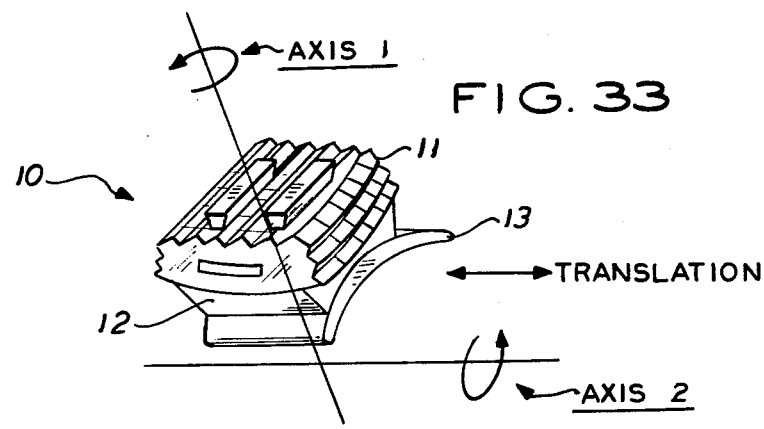
FIG. 33 is a diagrammatic illustration showing the two and only two degrees of rotational freedom permitted by the joint prosthesis of the present invention.

Referring now to FIG. 33, there is shown a diagrammatic illustration of the manner in which the ankle prosthetic joint 10 of the present invention provides only two degrees of freedom of rotational movement between the tibia and talus bones. More specifically, relative rotational movement is permitted between the tibial component 11 and bearing insert 12 with respect to the talar component 13 about Axis 1 and relative rotational movement is permitted between the tibial component 11 and bearing insert 12 with respect to the talar component 13 about Axis 2. Still more specifically, it will be noted and understood that no other degrees of freedom of rotational movement are permitted and hence improved joint stability is provided. Still further, it will be noted that in the context of only two degrees of rotational movement being permitted that Axis 1 and Axis 2 are not parallel.

It will be further noted that in this embodiment that medial-lateral translational movement of the tibial component 11 and bearing insert 12 with respect to the talar component 13 is permitted within the bony confines of the ankle mortise.

Referring now to FIGS. 34 and 35, there is shown a total knee joint endoprosthesis 60 embodying the present invention. More specifically, the knee prosthesis 60 comprises a pair of separate femoral components 62—62 for being fixtured to the femur such as by the integrally formed posts 64 and a suitable cement as discussed above with regard to fixturing. The femoral components 62—62 are provided respectively with condylar bearing surfaces 66—66 which jointly form a segment of a surface of revolution about the Axis 4 of FIGS. 34 and 35.

The knee prosthesis 60 further includes an intermediate bearing insert 68 provided with bearing surfaces 70—70 which are congruent with bearing surfaces 66—66 and which jointly form a segment of a surface of revolution about Axis 4. The intermediate bearing insert 68 is further providing with bearing surface 72 which is congruent with a bearing surface 74 provided on the tibial component 76 which may also be suitably fixtured to the tibia by integrally formed posts 78 and suitable cement as described above with regard to component-to-bone fixturing. The respective bearing surfaces 72 and 74 are congruent and permit relative rotation between the femoral component 62 and the intermediate bearing insert 68 with respect to the tibial component 76 about the axis 5.

It will be understood, as described with regard to the above embodiments, that the intermediate bearing element 68 may be suitably retained in the tibial component 76 by a suitable snap ring. Such retention of the intermediate bearing insert 68 in the tibial component 76 prevents relative axial movement of the intermediate bearing insert 68 with respect to the tibial component 76 and thereby provides increased stability of the joint. However, it will be understood that in certain embodiments the snap ring may not be necessary or desirable and therefore may be eliminated.

It will be further understood by those skilled in the joint prosthetic art that the prosthesis of the present invention may be embodied as a finger joint, elbow joint, wrist joint, and as a patello-femoral joint by making appropriate dimensional changes all within the teachings of the present invention.

Referring now further to prior art endoprostheses, and in particular to the prior art knee prostheses with patello-femoral replacement, it has been observed that such prior art prostheses have poorly designed patello-femoral interfaces in that they do not provide reasonably congruent area patello-femoral contact or sliding engagement over any appreciable range of knee motion. More particularly, such prior art prostheses typically produce contact stresses which result in the yielding and fatigue of the plastic bearing surface typically present in such prostheses. This is caused by the fact that the bearing surface of the femoral component over which the patella prosthesis must pass generally has several regions or segments of differing shape. For example, there is typically a fairly long, singly curved segment blending into a doubly curved segment blending again into a still different doubly curved segment. These varying segments or regions provide the femoral portion of the femoral-tibial articulation and those segments or regions do not have a common generating curve. Thus, when the patella prosthesis goes through its excursion over the femoral articular flange, the patella prosthesis meets a variety of surface contact conditions, namely, substantial portions of line contact, portions of point contact, and perhaps limited portions of area or congruent area contact. As is known, such line contact and point contact conditions generally produce excessive contact stresses which produce yielding and substantial wear of plastic prostheses. Hence, the extended wear life needed for successful prosthetic implantation is not provided.

Referring next specifically to typical prior art tibiofemoral knee prostheses, it has been observed that those prior art knee prostheses that allow axial rotation and medial-lateral motion in addition to flexion-extension motion have incongruent, usually theoretical point, contact between the femoral and tibial engaged bearing surfaces which produces excessive contact stresses leading to deformation and/or early wear and undesirably short prosthetic life. Wear products have also been shown in produce undesirable tissue reactions which may help induce loosening of the prosthetic components.

Those prior art knee prostheses that do provide congruent or area bearing contact fail to provide the needed axial rotation. This lack of axial rotation has been shown clinically and experimentally to result in deformation and loosening of tibial components and such prostheses no appear to be falling into disuse. However, as is known, a hinge type knee prosthesis does exist, i.e. the prosthesis shown in German Offenlegunsschrift No. 25 45 821, April 1976, which provides such axial motion by use of a trunion type tibial device and thereby provides both area contact and axial rotation. This prosthesis, however, is structurally distinct from the present invention in that it fails to allow unconstrained abduction-adduction by uncoupling of bearing surfaces associated with the flexion-extension action of the knee or by other means. Therefore, it fails to avoid the valgus-varus torque resulting from constraint of abduction-adduction thereby inducing loading into the prosthesis which has been shown to produce undesirable prosthetic loosening.

Current prostheses of both the hinge and dislocateable type such as the Geomedic knee replacement shown in U.S. Pat. No. 3,728,742 issued Apr. 24, 1973 to Averill et at. that produce area contact provide only one axis of rotation relative to the femur of the flexion-extension motion. Normal flexion-extension is however characterized by a polycentric flexion extrusion motion where rotation relative to the femur occurs about many axes. This polycentric motion allows for more efficient utilization of muscle forces by providing a posterior shift of the pivot when effective quadriceps action is important and an anterior shift when hamstrings effectiveness is important. Furthermore, in the human knee this polycentric action and the shape of the posterior condyles which influence this motion and allow full flexion capability for the leg. Failure to provide this polycentric motion thus tends to restrict muscle effectiveness and inhibit flexion. These restrictions tend to increase loading on the prosthesis and increase wear or likelihood of deformation or breakage and loading between prosthesis and bone tending to increase the possibility of component loosening.

It is further believed that loosening problems result from the direct attachment of plastic prosthetic components to bone through the use of relatively brittle cement that is weak in tension. Specifically, it has been demonstrated that even relatively thick plastic components when loaded in a normal fashion produce undesirable tensile stresses in acrylic cement which is commonly used to fixture such plastic components to bone. Such tensile stresses tend to produce bending of the plastic component which causes the ends of the plastic component to lift away from the bone as a result of the bending, thereby subjecting the bone-cement attachment to tension. As is known, cement has very poor tensile fatigue properties and the bone to which the plastic prosthesis is cemented appears to be adversely affected by tensile loads since normal bone loading is compressive. Accordingly, it is believed that these combined effects contribute substantially to prosthetic loosening problems and, specifically, it has been noted where clinical failure due to loosening occurs that it is almost always the plastic prosthesis component which loosens.

Figures 36, 37:
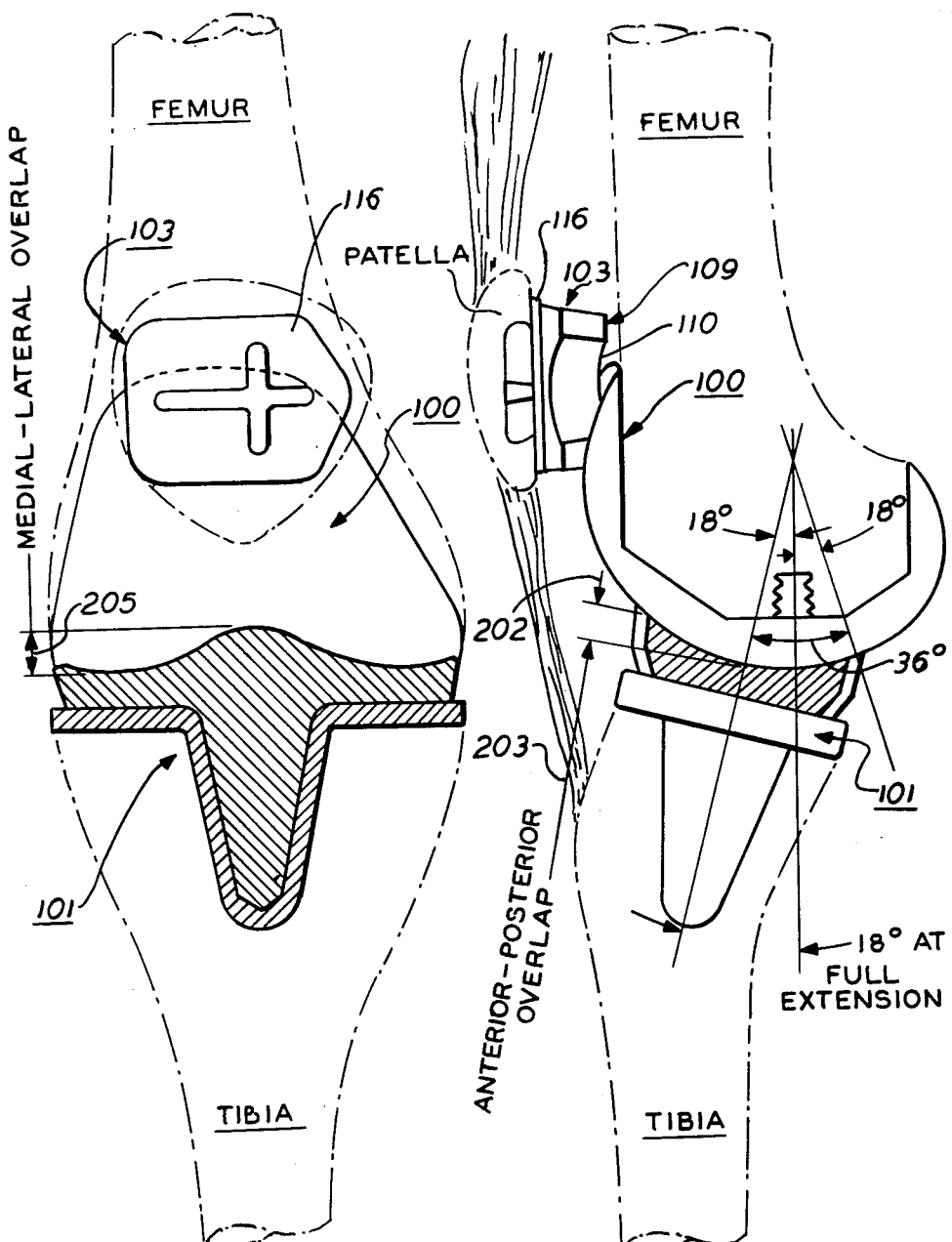

Another prior art prosthesis problem exists with regard to those knee endoprostheses for implantation in those cases wherein the cruciate ligaments are functionally absent but where the collateral ligaments are functional or are reconstructable. In the absence of cruciate ligaments, the prosthetic replacement must provide anterior-posterior knee joint stability so as to replace that stability lost by the lack of cruciates. Until recently most such cases were treated by a stable hingetype knee prosthesis which, unfortunately, appears to suffer from the loosening problems described above and furthermore typically produces substantial bone loss as a result of the relatively great bone resection required for implantation and necrosis of the bone caused by altered mechanical bone stresses. More recent attempts have been made to treat such cases with surface replacement prostheses such as the prostheses known as the Total Condylar and similar knee prostheses. However, these knee prostheses have theoretical point contact bearing surfaces with their above-noted attendant problems and, in addition, such prostheses tend to have instability and dislocation problems partially as a result of these point contact bearing surfaces. Referring now to FIGS. 36, 37 and 38 and to FIGS. 39 through 46, there is shown an endoprosthesis embodying the present invention which has been referred to as a tricompartmental knee prosthesis which includes the femoral component of prosthesis 100 best shown in FIGS. 39, 40 and 41; the patella prosthesis 103 comprising the intermediate patella bearing component 109 best shown in FIGS. 42, 43 and 44 and the patella fixturing component 116 shown in FIGS. 45 and 47; and the tibial prosthesis or component 101 comprising the tibial platform component 148 best shown in FIGS. 48, 49 and 50 and the intermediate tibial bearing component 139 shown in FIGS. 51, 52 and 53.

Generally, it will be understood that this tri-compartmental prosthesis includes three embodiments of the present invention, namely a first embodiment providing the patello-femoral articulation and comprised of the femoral component 100, the intermediate patella bearing component 109 and the patella fixturing component 116; a second embodiment providing the tibial femoral articulation and comprised of the femoral component 100, the tibial platform component 148, and the intermediate tibial bearing component 139; all as will be more fully understood as taught in detail below, and a third embodiment combining the other two embodiments. Additionally, the individual components are believed to be patentably novel.

Referring now to FIGS. 39, 40 and 41, there is shown in detail the femoral component 100 which includes, in the counter-clockwise anterior or posterior direction, a flange 100 formed integrally with two condyles 104—104. The femoral component 100 also includes a pair of fixturing posts; only one fixturing post, post 104a, being shown. The outside surface of the flange 102 provides most of the bearing surface for patella articulation. The condyles 104 are provided for replacing the condylar surfaces of the human knee. The bearing surfaces of 102 and 104—104 are referred to generally as the bearing surface 106. In accordance with the teaching of the present invention, the surface 106 in the counterclockwise anterior to posterior direction is a smooth, continuous surface formed by a series of segments of surfaces of revolution the respective shapes of which are generated or defined by rotating a common generating curve (generally identified as F) around a plurality of generating axes at respective pairs of major generating radii (or each at a respective major generating radius where the radii of each pair are equal) and through respective angles of rotation.

This common generating curve F is a smooth continuous plane curve and as may be understood from FIG. 39, the shape of which is defined by (i) two arcs K1 and K2 struck, respectively, by two radii A1 and A2 from respective centers H1 and H2 separated by a distance X; (ii) two lines 107 and 108 respectively tangent to the arcs K1 and K2 and at angles $\alpha 1$ and $\alpha 2$, respectively, with respect to a line G tangent to arcs K1 and K2; and (iii) an arc K3 struck by radius B from center H3 and wherein arc K3 is also tangent to the tangent lines 107 and 108.

Figure 63:
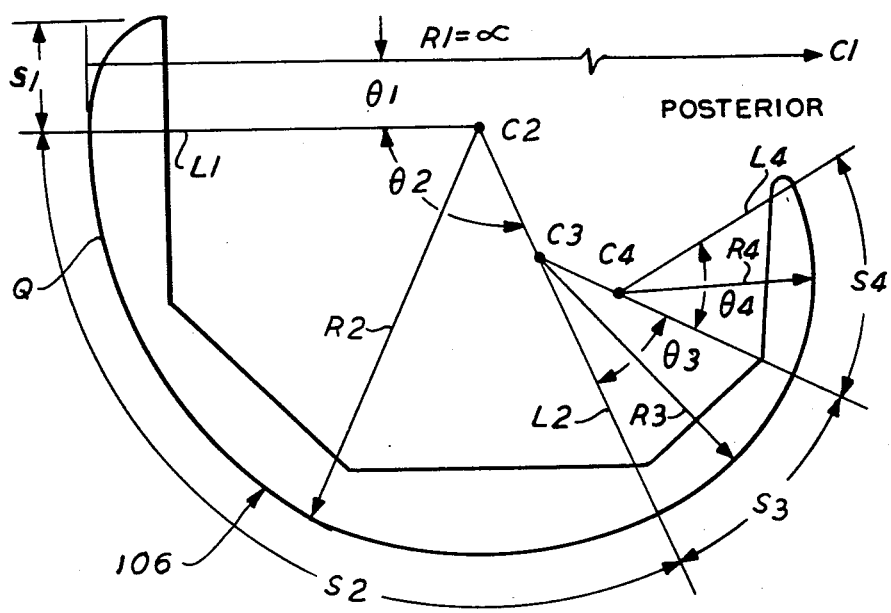
FIG. 63 is a diagrammatic illustration showing the manner in which the common generating curve of FIG. 62 is rotated about the respective axes to generate the segments of surfaces of revolution defining the shape of the femoral bearing surface of the alternate embodiment of the present invention embodied as a knee prosthesis.

Referring now to FIG. 63, where a further understanding of the general teachings of the present invention is illustrated, it will be understood that the shape of the bearing surface 106 (FIG. 39) is defined or generated by a series of segments of surfaces of revolution each of which segments is defined or generated by rotating the common generating curve F around a respective generating axis at respective pairs of major generating radii (or each at a major generating radius where the radii of each pair of major generating radii are equal) and through a respective angle of rotation. In generating each segment of a surface of revolution, the common generating curve F is oriented with respect to a generating axis by a pair of major generating radii D1 and D2 which are the respective distances (shortest distances) from points M1 and M2 where the common generating curve F contacts tangent line G.

Figure 62:
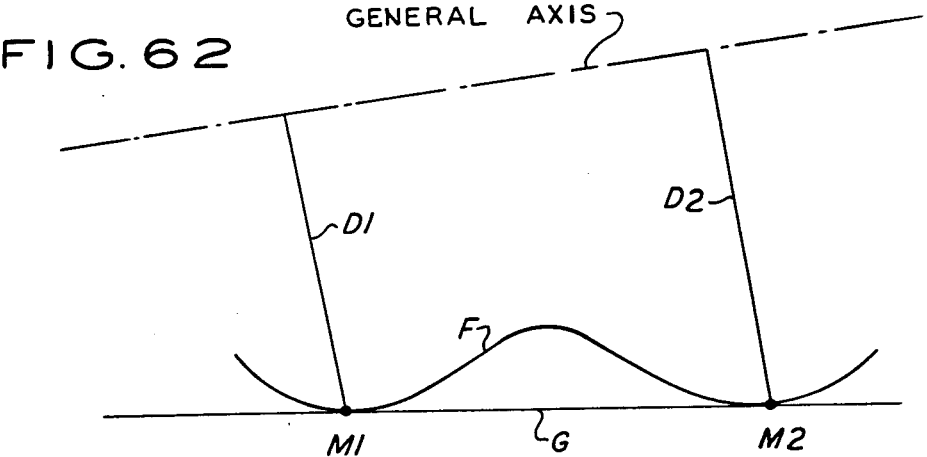
FIG. 62 is a diagrammatic illustration showing the manner of rotation of the common generating curve of the present invention.

Referring now to FIG. 63, it will be understood that this figure is a diagrammatic illustration showing the manner in which the series of segments of surfaces of revolution S1, S2, S3 and S4 defining the shape of the bearing surface 106 are generated and where the curve Q represents the trace of points M1 and M2 as viewed along line G (FIG. 62) resulting from the rotations about the respective generating axes generating the surface segments. It will be further understood that the shape of the bearing surface 106 is defined by a series of segments of surfaces of revolution where each pair of major generating radii D1 and D2 for generating each segment decrease in length respectively as rotation of the generating curve F proceeds about each generating axis in the counterclockwise anterior to posterior direction as viewed in FIG. 63. In the present embodiment and as illustrated in FIG. 62, the pairs of major generating radii D1 and D2 are equal in each instance and may in each instance be replaced by a single major generating radius R (i.e. R1, R2, R3 and R4) as shown in FIG. 63. In this embodiment, the bearing surface 106 consists of four segments of surfaces of revolution S1, S2, S3 and S4.

S1 is generated by rotating the common generating curve F through an angle $\theta 1$ about generating axis C1 perpendicular to the plane of FIG. 63 at a major generating radius R1. In the present embodiment, R1 is equal to infinity and since only the patella intermediate bearing component 109 of FIGS. 30, 40 and 41 articulates with segment S1, it will be referred to as the patella-femoral bearing surface segment.

Segment S2 is generated by rotating the common generating curve F through an angle $\theta 2$ about generating axis C2 parallel to C1 at a major generating radius where R2 is equal to radius A1 which is equal to A2 in FIG. 39; since such radii are equal, it will be understood that segment S2 is a spherical surface of revolution. For continuity and smoothness of surface 106, axis C2 must lie on the ray L1 passing through C1 and defining the end of segment S1. This segment (S2) is of special importance since both the patella and tibial intermediate bearing components 109 and 139, respectively, articulate with this segment and since the greatest loads on these components during normal walking occur when they articulate against this femoral bearing segment. This segment (S2) will, therefore be referred to as the primary load bearing surface segment.

Segment S3 is generated by rotating the common generating curve F through an angle $\theta 3$ about generating axis C3 parallel to C2 located at major generating radius R3 where R3 is less than R2. Again, for continuity and smoothness of surface 106, axis C3 must lie on ray L2 passing through C2 and defining the end of segment S2.

Finally, segment S4 is generated by rotating the common generating curve F through an angle $\theta 4$ about generating axis C4 parallel to C2 located at major generating radius R4 which is less than R3. Again for continuity and smoothness of surface 106, axis C4 must lie on ray L3 passing through C3 and defining the end of segment S3. These latter two segments will be referred to, respectively, as the first and second posterior femoral bearing surface segments respectively.

Referring again to FIG. 40, it will be understood that FIG. 40 is a side view of an actual embodiment of the present invention as shown if FIG. 39 and that the segments of surfaces of revolution S1, S2, S3 and S4 shown in FIG. 63 are also shown in FIG. 40 at their respective locations.

In one embodiment of the present invention, the respective angles $\theta$ and each respective major generating radius were as follows:

| SEGMENT | $\theta$ DEGREES | MAJOR GENERATING RADIUS R/in |
|---|---|---|
| S1 | 0 | ∞ displacement .612" |
| S2 | 107¾ | 1.388 |
| S3 | 62¼ | .801 |
| S4 | 62 | .578 |

Referring again to FIGS. 40 and 63, it will be noted that the generating axes C1, C2, C3 and C4 are parallel with respect to each other and it will be understood that the tangent line G is oriented substantially parallel to the generating axes, however, in accordance with the teachings of the present invention, such need not be the case and the generating axes may be oriented other than parallel with respect to each other and, as shown in the general case illustrated in FIG. 62, the tangent line G may be oriented with respect to the generating axes other than parallel.

Referring again to the patella prosthesis and in particular to the intermediate patella bearing component 109 of FIGS. 42, 43 and 44, it will be understood that in accordance with the further teachings of the present invention such intermediate bearing component provides a load bearing surface indicated by general numerical designation 110 for engaging the bearing surface 106 of femoral component 100 and which load bearing surface 110 includes a primary load bearing surface segment 111, a pair of secondary load bearing surface segments 112 and 114 and a pair of transition segments 112a and 114a between 111 and 112 and 111 and 114 respectively. Further, it will be understood in accordance with the teachings of the present invention that the shape of the load bearing surface 110 of the patella intermediate bearing component 109 is defined or generated by the common generating curve F used to generate the segments S1-S4 of the femoral bearing surface 106. Referring to FIG. 43, it will be understood that the common generating curve F is rotated through an angle $\theta 5$ (in one embodiment angle $\theta 5$ equalled 20°) about generating axis C5 at the pair of major generating radii D1 and D2 shown in FIG. 62 where D1 and D2 are equal and are equal to major generating radius R2 shown in FIG. 63, to define the shape of the primary load bearing surface segment 111. Therefore, the patella primary load bearing surface segment 111 congruently matches the primary load bearing surface segment S2 of femoral bearing surface 106 and upon articulating therewith engages the primary femoral bearing surface segment S2 in sliding area contact. The secondary load bearing surface segments 112 and 114 of the patella bearing surface 110 of FIG. 43 likewise match the patella femoral bearing surface segment S1 of surface 106 of FIG. 40 and hence their shapes are defined or generated by rotating the common generating curve F about an axis C9 at infinity parallel to axis C5 as was done in generating the shape of segment S1 of femoral bearing surface 106. Therefore, the patella prosthesis secondary load bearing surface segments 112 and 114 congruently match the patello femoral bearing surface segment S1 of femoral bearing surface 106 and upon articulating therewith engage the femoral bearing surface segment S1 in sliding area contact. The transition segments 112a and 114a defined by rotating the common generating curve F through angles $\theta 7$ and $\theta 8$ about axes C7 and C8 respectively at a pair of negative generating radii (directed to opposite sides of common generating curve F from those shown in FIG. 62) both about 0.30 in. in one embodiment. These transition segments 112a or 114a engage in line contact segments S2 and S1 of the femur near their interface as the contacts shift between segment S2 of the femur with the primary load bearing segment 111 to contact between femoral segment S1 and the secondary load bearing segments 112 and 114.

Figure 64:
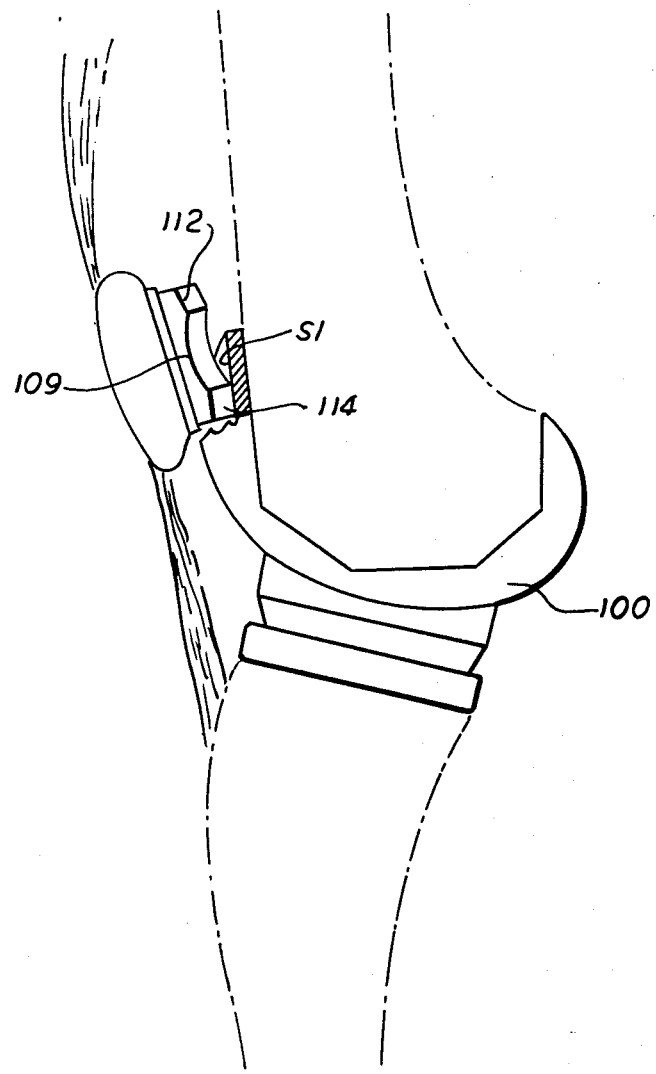
FIG. 64 is a diagrammatic illustration showing articulation between the patella prosthesis and the femoral component of an alternate embodiment of the present invention embodied as a knee prosthesis.

In another embodiment of the patella prosthesis of the present invention, the segments 112 and 114 are inclined downwardly with respect to the horizontal as viewed in FIG. 43 to better accommodate the orientation of the patella prosthesis with respect to the femoral prosthesis during full extension of the human knee as shown in FIG. 64 and therefore provides a more uniform load distribution on the secondary load bearing surface segment 112 or 114.

Figure 56:
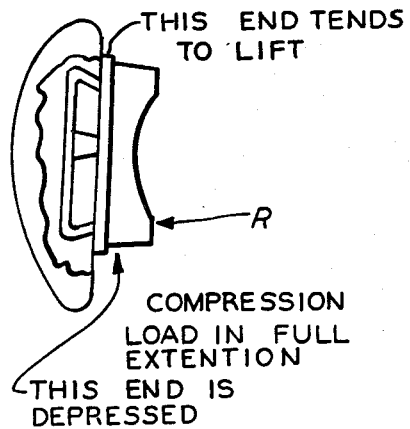
FIG. 56 is a diagrammatic illustration showing tipping loads on a patella prosthesis.

The patella intermediate bearing element 109 is retained on the remnant of the human patella by use of the patella fixturing component 116 of FIGS. 45 and 47 which fixturing component may be suitably fixtured to the remnant human patella by use of an acrylic grouting agent or cement by crossed fixturing fins 117 and 118 on the dorsal side of the metal plate 120. Such fixturing fins resist tipping loads, as shown in FIG. 56, and, in addition, provide a reinforcing effect which allows the use of a thin plate 120 which is desirable, since one wishes to minimize the change in overall patella thickness resulting from prosthetic replacement so as not to adversely affect patella function, skin closure after surgery and cosmesis. The fins and metal plate reinforce and strengthen the patella remnant and minimize the possibility of its fracture. The opposite or ventral side of plate 120, FIG. 45, which comprises the bulk of the secondary fixturing component bearing surface which mates with the secondary bearing surface 128 on the patella intermediate bearing element 109, is provided with a button 122 which retains the patella intermediate bearing element on the patella fixturing component 116 with a snap fit. As shown in FIGS. 45 and 46, the outer diameter of the button 122 is formed from a curve with two tangent radii which produce a smooth retaining male surface 122a when mated with a correspondingly shaped female surface 124 (FIG. 42) provided on the patella intermediate bearing element 109. These shapes allow easy entry of the male into the female member without producing permanent deformation resulting from conventional snap-fit configurations. The mating conical sections provide additional secondary compressive and thrust bearing surfaces. The button 122 is provided with a generally conical shaped bearing surface 126 for rotatably engaging the correspondingly shaped conical secondary bearing surface 128 of FIG. 42 provided on the patella intermediate bearing element 109 in congruent or area rotational engagement to permit rotation of the patella with respect to femoral bearing surface 106 and the distal end of the femur about axis A8 (FIG. 38).

Further, and referring to FIG. 45, the patella fixturing component 116 of FIG. 45 is provided with a pin 130 for engaging a corresponding, curved slot 132 formed in the intermediate patella bearing component 109 (FIG. 42) to limit the relative rotation between intermediate patella component 109 and the patella fixturing component 116 and thereby prevent disorientation between the intermediate patella component 109 and the femoral component 100 during implantation and subsequently during actual use. Further this limited rotation has been found to be reasonably necessary since effusion (built up of blood) post-operatively may temporarily lift the patella primary bearing surface 110 of the patella intermediate bearing element 109 free of the restraining effects of the femoral component 100.

It will be further noted, as shown in FIGS. 42–47 that the patella intermediate bearing component 109 and patella fixturing component 116 are made symmetrical about a plane passing through the center of the primary load bearing segment 111 and through the generating axis C5 producing segment 111, so as to allow the use of the same patella prosthesis in either the right or the left knee. It is for this reason that two rather than one secondary load bearing segments (112 and 114) are provided on the bearing surface 110.

Figure 54A:
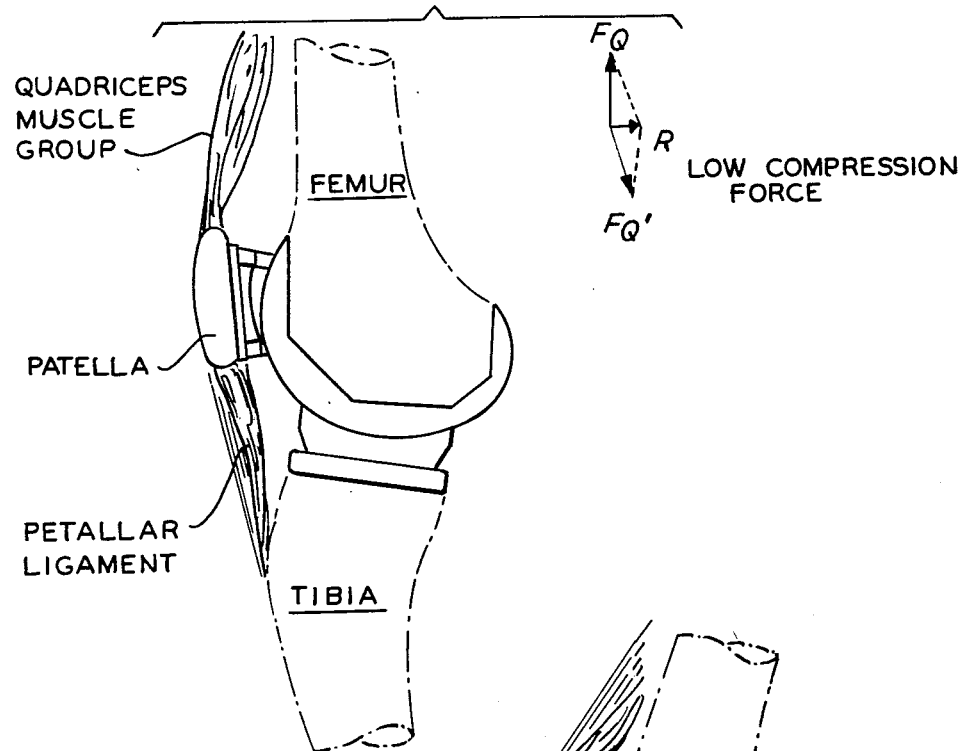
FIGS. 54A, 54B and 54C are composite diagrammatic illustrations showing the various compressive forces present in a knee provided with the knee prosthesis.
Figure 54B:
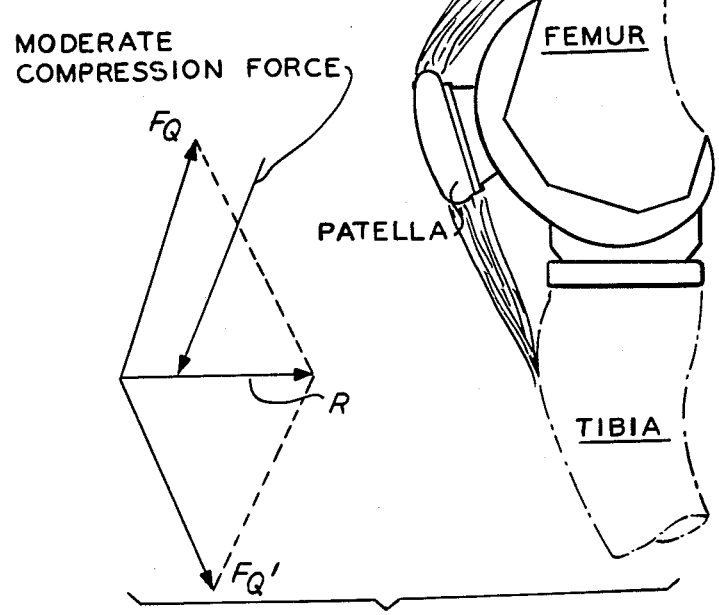
Figure 54C:
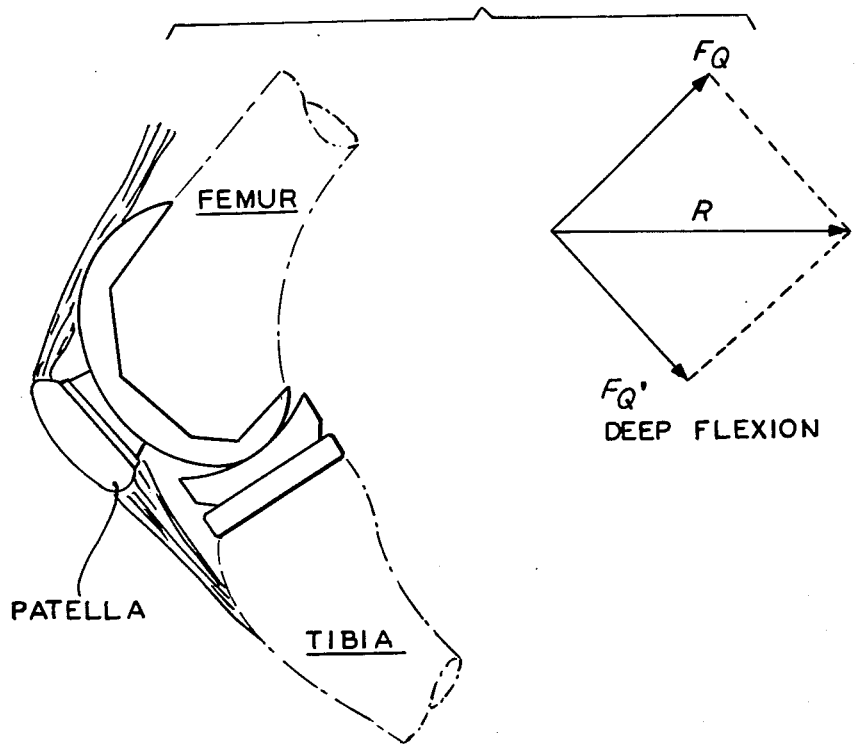

Referring now to FIGS. 54A–54C, there is illustrated diagrammatically, the manner in which the patello-femoral portion of the tricompartmental prosthesis provides area or congruent sliding contact between the bearing surface 106 of the femoral component 100 and the bearing surface 110 of the patella-intermediate bearing element 109 over the important phases of the range of motion commonly experienced by the human knee and provides line contact between such bearing surfaces only during a brief transitional phase. Referring first to FIG. 54A, it will be noted that at full knee extension the quadriceps muscle groups provides a quadriceps force $F_Q$ which in normal activities is quite low at full extension and because of the orientation of the force $F_Q$ the resultant patello-femoral compression force R of FIG. 54A is only a small fraction of force $F_Q$. During this phase of human knee action there is area contact between the bearing surface segments S1 and 112 and 114 of the femoral and patella components, respectively, see FIGS. 40 and 43.

Referring now to FIGS. 54B and 54C wherein the load bearing stance phase experienced during the normal walking cycle is illustrated diagrammatically, it will be noted here the quadriceps force $F_Q$ is greater and hence the resultant patello-femoral compression force R is much greater than at the full extension illustrated in FIG. 54A by virtue of the greater quadriceps force $F_Q$ and the smaller included angle between the quadriceps force $F_Q$ and the patella ligament force $F_{Q'}$. Of course, as is known, even greater flexion angles are experienced by the human knee during stair climbing and descent and hence at these times even greater patella bearing resultant forces R occur.

It will be understood that during the short transition phase in moving from segment S1 to segment S2 that transition segments 112a or 114a of the patella bearing surface 110 is in sliding line contact with the femoral bearing surface 106. As is further known, during the most common and hence most important human knee activity, namely level walking, there is no substantial quadriceps activity or force present until approximately 10° of knee flexion is achieved at which the patella articulation of the prosthesis of the present invention has just entered the primary load bearing surface segment S2 wherein there is sliding area contact between the femoral bearing surface segment S2 and the patella primary load bearing segment 111. Thus, the above-noted transitional and hence momentary line contact is not of serious concern since at this time the quadriceps force $F_Q$ is essentially negligible and even if it were substantial the resultant compression force R would still be quite low by virtue of the large included angle between forces $F_Q$ and $F_{Q'}$. Area or contact is only needed during the walking load bearing and other activity phases where compression forces R are significant.

The regions S1 and S2 on the femoral component and corresponding transition segments 112a or 114a and the primary and secondary load bearing segments 111 and 112 or 114 are needed to produce anatomical patella femoral articulation wherein at full extension as the superior aspect of the patella lifts off the femur as in FIG. 54A and yet allow central area contact engagement at moderate and full flexion as shown in FIGS. 54B and 54C.

Referring now to FIG. 54C, wherein deep knee flexion is illustrated diagrammatically, it will be seen that it is during deep knee flexion that the patello-femoral compression load R is highest. It will be understood, and as illustrated in FIG. 54C, the patella bearing surface 110 (FIG. 43) articulates with the same surface segment S2 (FIG. 40) wherein the tibial femoral articulation occurs during full extension, thus, the primary load bearing surface segment S2 of surface 106 supplies the femoral bearing surface for both articulations (patello-femoral and tibio-femoral articulations) at times of greatest loading during the walking gait cycle and this commonality is a significant feature of the present invention. Of course, as known to those familiar with the anatomy of the human knee, this situation (common articulation between a portion of the human condyles and both the patella and tibial bearing surfaces) does not occur.

Figure 55:
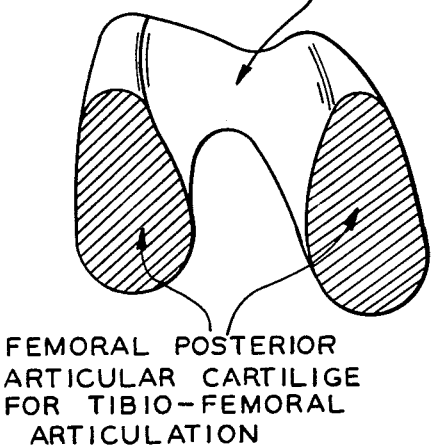
FIG. 55 is a view of the distal femur of a human being.

As shown in FIG. 55, in the human knee the femoral anterior articular cartilege against which the human patella articulates is distinct from that which articulates with the tibia. Such natural structures adapt during development of the human knee to produce precise mating of the structural and articulation elements of the knee but such precision of mating is not practical in replacement knee prostheses because of the large individual variations found in different human knees and the manufacturing and surgical difficulties involved in producing such precision. Thus, the use of a common femoral prosthesis primary load bearing surface segments S2 for both the patella and tibial articulations represents a significant feature in providing the needed sliding area engagement or congruency of articulation for extended wear life.

Referring again to FIG. 42, it will be noted that the depth of engagement of the patella bearing surface 110 into the femoral bearing surface 106, distance T shown in FIG. 42, is substantial and hence allows substantial subluxation resistance to side thrust loads. It has been found that in individuals where this dimension is small or excessive knee valgus is present, subluxation of the patella is common. Yet in many known prior art devices, the corresponding depth of engagement provided is inadequate or non-existent. Further, and referring again to FIGS. 42 and 45, it will be noted that area rotatable mating fit (bearing surfaces 128 and 126) between the patella intermediate bearing insert 109 and the patella fixturing component 116 allows rotation therebetween and this rotation is highly desirable to accommodate possible surgical misalignment during implantation and the small naturally observed patella rotation with respect to the human femur during flexion-extension movements.

Referring now to FIGS. 51, 52 and 53, and to the intermediate tibial bearing component 139 shown therein, this component provides a primary load bearing surface 140 on its superior side and a second bearing surface 142 on its inferior side. The primary load bearing surface 140 is also formed as a surface of revolution and its shape is defined or generated by the common generating curve F used to generate the shape of segments S1–S4 of femoral bearing surface 106 and the shape of patella bearing surface 110.

Referring now to FIG. 52, it will be understood that the shape of the primary load bearing surface 140 is defined by rotating the common generating curve F through an angle $\theta_6$ (in one embodiment of the present invention .$\theta_6$ equalled 70 degrees) about generating axis C6 at the same major generating radii D1 and D2 shown in FIG. 62 where D1 and D2 are again equal and equal to R2 shown in FIG. 63. Therefore, the tibial primary load bearing surface 140 congruently matches the primary load bearing surface segment S2 of femoral bearing surface 106 and upon articulating therewith engages the femoral primary bearing surface segment S2 in sliding area contact. Therefore, congruent articulation is provided at the tibial-femoral joint interface for approximately 36 degrees of knee flexion wherein the greatest loads during the walking cycle are experienced as indicated in FIG. 54B. The 0 to 95 degree flexion-extension range includes almost all strenuous activities in which an individual with an endoprosthesis is likely to engage. Articulation in the 35–95 degree range occurs in the first posterior femoral bearing segment S3 of FIG. 40 and hence there is line contact as indicated in FIG. 54C. Although such line contact or incongruity is less desirable than sliding area contact, it produces acceptably low contact stresses while allowing sufficient flexion necessary for normal activities since loads during walking in this phase of flexion are much less than in the 0–36 degree range or area contact phase. Heavy joint loading in this range of knee motion occurs much less frequently than in the 0 to 36 degree range and thus higher periodic or transitional stresses can be tolerated without producing fatigue or excessive wear. Flexion from 95 degrees to 140 degrees is accommodated by the second posterior femoral bearing segment S4 of the femoral prosthesis and expected stresses at such flexion angles are such that serious permanent deformation is not anticipated except perhaps during deep knee bend excercises such as deep squats which should be avoided by anyone having any knee prosthesis. Fatigue is not of concern here (segment S4) since the expected frequency of occurrence of these stresses is low. Obviously, a patient with such knees should be strongly encouraged not to perform deep knee bend or similar exercises. It should be noted that few knee prostheses allow in excess of 90 degrees of flexion and those that do, while still allowing reasonable axial rotation, experience far greater contact stress than the present invention. The last region is provided to allow the extreme flexion range which is often needed during sitting where small loads on the knee are experienced.

The two incongruent or line contact phases of contact associated with segments S3 and S4 are provided in order to provide nearly normal flexion and extension motion by providing a reasonable approximation to normal condylar geometry. Incongruency in these phases occurs only in one dimension rather than two dimensions as in most prior art prostheses. Thus, normal motion is provided while keeping contact stress within acceptable limits of most normal activity.

The second bearing surface 142, FIGS. 51, 52 and 53, is on the inferior side of the intermediate tibial bearing component 139. This bearing surface is comprised of a flat surface 143 and a projecting conical surface 144. The flat and conical bearing surfaces engage the superior surface 145 of the tibial fixturing component 148 shown in FIGS. 48, 49 and 50, and the conical surface 150 therein in area contact and provides rotation about a single axis, i.e. axis A7 of FIG. 38 to permit axial rotation of the tibia with respect to the femur.

The shape of the plate section 152 of the tibial platform component 148 is contoured so as to engage, where practical, the outer cortical bone of the tibia so as to improve load bearing and to allow this component to be used for both right and left tibias. A short spike 153 which helps distribute joint loads and supplies additional load transfer to the cortical bone on its posterior aspect is used for improving load bearing.

It will be understood that the double symmetry of both tibial components 139 and 148 eliminates the need to designate an anterior or posterior aspect of these components, as well as the right or left knee aspect, and thus eliminates the concern of the implanting surgeon with these matters during implantation.

Figure 57:
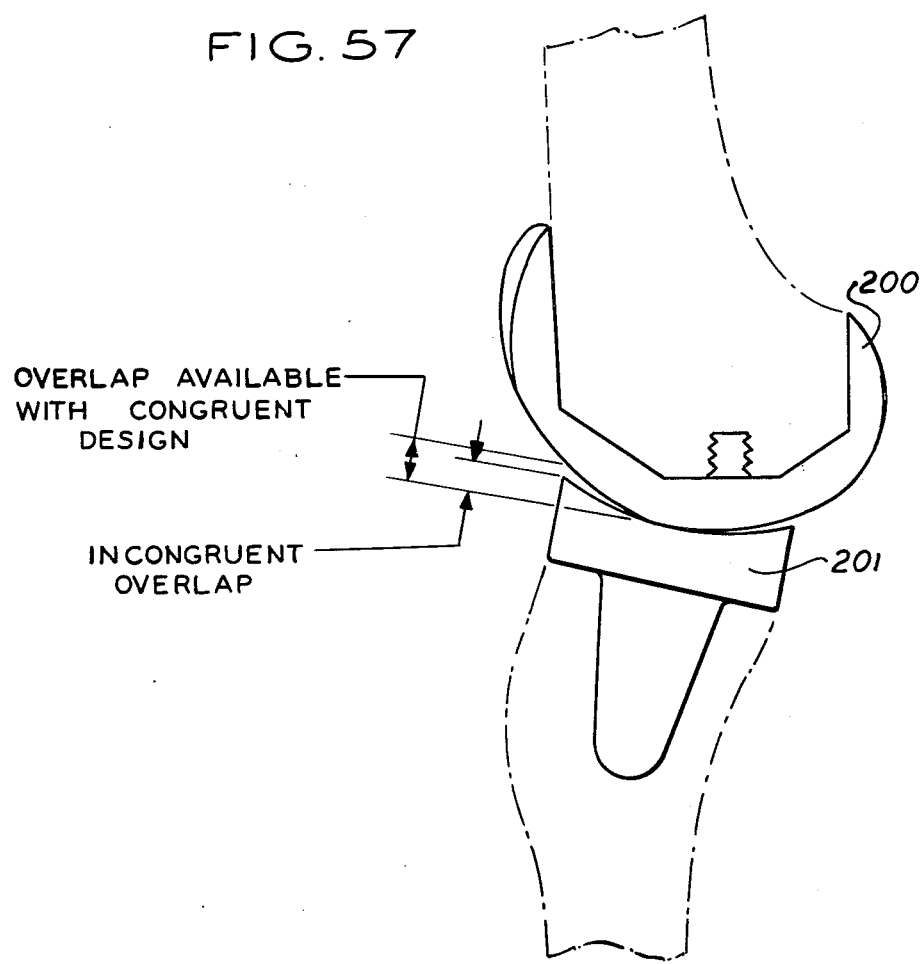
FIG. 57 is a diagrammatic illustration comparing the overlap available between a prosthesis having congruent design and a prosthesis having incongruent design.

It will be further understood by those skilled in the art and referring again to the femoral component 100 and the patella prosthesis 103, that the bearing surfaces 120 and 126 of the patella fixturing component 116 and bearing surfaces 128a and 128 of the intermediate patella component 109 accommodate both axial surgical misalignment and normal rotation while permitting area contact between the bearing segments S1 and S2 of the femoral component 100 and the bearing surface 110 of the intermediate patella component 109. Similarly, it will be further understood that the bearing surfaces 143 and 144, respectively, of the intermediate bearing component 139 and the bearing surfaces 145 and 150 respectively of the tibial platform component 148 accommodate both axial surgical misalignment and normal rotation while permitting sliding area contact between the primary load bearing segment S2 of femoral component 100 and the primary load bearing surface 140 of the intermediate tibial bearing component 139. This congruence is provided in the important stance phase of walking illustrated diagrammatically in FIG. 54B. This congruence or area contact also has an additional advantage, namely, it provides greater anterior posterior stability by providing greater overlap as illustrated diagrammatically in FIG. 57. It will be understood that the incongruity illustrated in FIG. 57 reduces the overlap dimension and thereby reduces anterior-posterior stability. In the case of congruity, this overlap is further reduced by rotation of the femoral component 200 with respect to the tibial component 201 as a result of normal walking or surgical misalignment.

The present invention, as embodied for providing the tibio-femoral articulation, and as illustrated in FIG. 37, provides great anterior-posterior stability by virtue of its congruency or area contact which provides the greater overlap dimension shown by the arrows 202 and 203 of FIG. 37, and anterior-posterior stability if further provided by avoidance of rotation between the tibio-femoral bearing surfaces 140 and 106 (rotation being provided between the surfaces 143 and 145, respectively, of the tibial intermediate bearing component 139 and the tibial platform component 138).

Further, and as will be understood by those skilled in the art, greater medial-lateral shear stability is provided by the present invention due to the deep engagement between the femoral component 100 and the tibial prosthesis 101 as illustrated by arrow 205 of FIG. 36.

Figure 59:
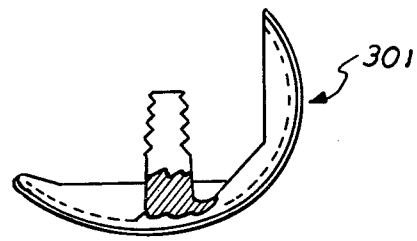
Figure 58:
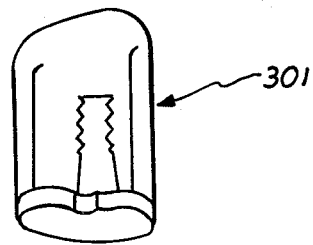

Referring now to FIGS. 58 and 59 and FIGS. 60 and 61, there is shown a bicompartmental embodiment of the present invention utilizing a pair of individual femoral components 301 and 302 and, as illustrated diagrammatically in FIGS. 60 and 61 omits the use of the patella prosthesis 103. Referring specifically to FIGS. 58 and 59, there is shown therein a right individual femoral component 301 and it will be understood that the individual femoral component 302 shown in FIGS. 60 and 61 is the mirror image of the femoral component 301 shown in FIGS. 58 and 59. Tibial prosthesis 101 of this embodiment is the same as the tibial prosthesis 101 described above. It will be understood, and referring to FIG. 61, that the individual femoral components, e.g. 302, are provided with a load bearing surface 306 which is identical to the segments S4, S3, and a major portion of the primary load bearing segment S2 shown if FIG. 40. Thus, it will be further understood that segment S2 of these individual femoral components 301 and 302 are in area contact with the primary load bearing surface 140 of the tibial component 101 as taught above and thus provides the same tibio-femoral articulation as described above.

Referring again to FIGS. 51, 52 and 53, it will be still further understood by those skilled in the art that the intermediate tibial bearing component 139 may be easily removed intraoperatively to allow replacement of this component with an intermediate tibial bearing component having a thickness providing proper ligamentous (collateral ligments) tension.

Thus, a number of intermediate tibial bearing components of varying thicknesses may be provided so that the implanting surgeon may shim for proper ligamentous tension without disturbing fixtured components, e.g. tibial platform component 148 and femoral component 100. Further, such structure allows easy replacement of the intermediate tibial bearing component 139 in the event of unusual or unexpected wear or deformation. Similarly, this is true with respect to the patella prosthesis 103 wherein the intermediate patella bearing component 109 may be of varying thicknesses and replaceable in the event of unusual or unexpected wear or deformation.

It will be further understood that the femoral component 100, the patella fixturing component 116, and the tibial platform component 148 may be made preferably of a surgical metal such as cobalt-chromium alloy or titanium or stainless steel but may be made of any relatively rigid material (compared with the grouting agent) that is biocompatible, capable of withstanding the applied loads, and processes adequate bearing properties against the intermediate bearing inserts, e.g. the intermediate patella bearing component 109 and intermediate tibial bearing component 139 may be made of any biocompatible material strong enough to withstand loads and adequate in bearing against the material with which it is engaged, but is preferably made of a plastic such as ultra high molecular weight polyethylene or compolymer acetal.

KNEE ENDOPROSTHESIS SURGICAL IMPLANTATION PROCEDURE

The patient is placed in a supine position on the operating table. The knee is prepared and draped in a sterile fashion. A thigh tourniquet previously applied is inflated to 400 mm Hg after elevation of the leg for one minute to allow for venous run-off.

The knee is fully extended and a gently curved S-shaped incision is made on the tibial tubercle up towards the medial border of the patella tendon, then curving posteriorly along the medial border of the vastus medialis.

The medial retinaculum, capsule and synovial layer are incised in line with the skin incision. The vastus medialis muscel belly is elevated free from its attachment to the adductor magnus tendon. The patella is reflected laterally exposing the entire tibio-femoral joint. If there is excessive tension in the quadriceps mechanism preventing complete lateral displacement of the patella, then sharp detachment of the medial ¼ of the patella tendon from the tibial tubercle may be necessary. In a similar fashion, further blunt disection of the medial attachment of the vastus medialis may be needed to mobilize the quadriceps mechanism proximally. These maneuvers will allow complete flexion of the knee to 110 degrees with complete anterior exposure of the joint.

At this time, excision of hypertrophic synovium and redundant fat pad is performed. Medial and lateral menisectomy will facilitate exposure of the tibial plateau borders and should be performed. Examination of the intercondyler contents will reveal the condition of the cruciates. Redundant synovium should be excised from this region to prevent possible impingement or overgrowth onto the tibial component surface.

With the proximal tibial and distal femus cleared of soft tissue debris, bone guards are slid posteriorly between the collateral ligaments and the posterior capsule to protect the posterior neurovascular bundle during resection of the articular surfaces. A ¾" periosteal elevator may be used to develop the soft tissue planes for the bone guards, which also serve as knee retractors.

The knee is flexed to 100 degrees and a drill hole at the intercondyler notch border is made with a ¼" drill. The drill is taken down to the level of the posterior femoral shaft. Next, a tibial resection jig is placed with a spike located on the posterior aspect of the femoral shaft and a distal limb of the instrument parallel to the tibia. With the collateral ligaments in tension during this flexion phase, a proper resection plane is insured by use of the parallel cutting slots available in the jig. The jig has an automatic 10 degree retroversion angle insured when the knee is flexed parallel to the distal limb of the jig. Using an oscillating saw, the tibial preparation is made. The resection planes are made at 5, 10, or 15 mm, depending upon the amount of bone stock available for perpendicular loading of the tibial component. Once the proper flexion tension has been achieved and the bone resection has been made, the tibial alignment jig is removed from the femoral shaft and the femoral shaper is next replaced into the same channel. The femoral shaper is situated such that the anterior and posterior cuts are symmetrically parallel to the femoral condyles. Using again an oscillating saw in these cuts, the anterior surface and posterior condyles of the femur are resected. The knee is then brought into full extension after removal of the femoral shaper and an extension femoral alignment jig is placed into the joint. With manual traction on the femur and aligning an adjustable valgus guide into 5 to 10 degrees of physiologic valgus, the horizontal cut on the distal femur is made to insure adequate extension tension of the collateral ligaments. Once this cut has been made using the oscillating saw, the extension alignment jig is removed from the knee joint. The knee is again flexed and an oblique osteotomy jig is replaced into the fixturing hole and using a mallet impacted into the distal femoral bone stock. The anterior and posterior oblique cuts are then made in line with the jig surface and a central notch of the oblique osteotomy jig is used to trim away the boney surface for the anterior femoral flange. The oblique osteotomy jig is removed and the alignment holes made by the jig are curetted out to accept the fixturing pins of the femoral prosthesis. A trial fit of the femoral component is next made. Excessive bone stock is trimmed to insure proper contact of all surfaces. Next, the tibial preparation is completed. A marking template is used to mark out the central spike position. Following marking with methylene blue, central spike channel is fashioned using a curette or gouge. A trial seating of the tibial component is next made and proper bone resection is performed at this time to insure excellent metal to bone contact of the prosthesis. With resections of both bones now finished, the trial reduction of the tibial and femoral components is made as follows:

The metal tibial component is placed in its central spike channel and the appropriate intermediate bearing component is inserted into place. Next, the femoral component is placed in its proper position and the knee joint is tested in both flexion and extension for proper ligamentous tension. If resection cuts have been made properly, there should be no gross instability. Should mild laxity exist in flexion and extension, then thicker bearing components may be used to tighten the collateral ligaments. The bearing heights come in 2.5 mm increments and may be used to finely adjust the ligamentous tension at this stage. Once the tibial-femoral resections have been properly prepared, attention is given to the patella replacement. Using a scalpel, the synovial tissue and retinaculum are freed from the periphery of the patella down to the level of the patella tendon. A reciprocating saw is then used to remove the articular surface. The plane of the cut should parallel the inferior surface of the patella tendon.

A patella marking template is now centered over the horizontal and vertical axis of the patella with the long fixturing fin directed toward the lateral aspect. Methylene blue dye is used to mark the fin channels for the fixturing fins of the component. These channels are taken to a depth of ¼" and undercut for mechanical locking of the cement.

The trial patella replacement can now be seated to assess the fit. Any boney impingement is removed to insure proper seating. The patella is reflected to its anatomical position to check the alignment in the femoral track. A range of motion may now be tested with all three components in place. The patella prosthesis should center in the femoral track and easily glide along the femoral flange without binding. Restricting adhesions or boney impingement should be completely corrected at this time.

The components are removed after a satisfactory trial fit and the wound is thoroughly irrigated with antibiotic saline solution. The first batch of methylmethacrylate is mixed and placed on the tibial surface with the knee in the flexed position. The tibial component is gently slid into its fixturing channel and firmly held in compression until completely polymerization has been obtained. During the setting phase, excess methylmethacrylate may be trimmed using a scalpel and curette from the edges of the tibial component. Next, the bearing component is placed into the tibial component and the femoral component is cemented in place. Excess methylmethacrylate is removed from around the femoral component to insure that the bearing surface will remain free of this abrasive agent. With a third batch of methylmethacrylate, or else using a portion of that cement used for the femoral component, the cancellous patella bed is covered. The patellar component fixturing fins are firmly pressed into their mating channels and the component is held tightly with a patellar component clamp. Excess methylmethacrylate may now be removed from the edges of the patella backplate. Upon complete polymerization of all cement beds, a range of motion is again tested after returning the patella to its anatomical position. Two medium sized hemovac drains are now placed in the joint space and brought to exit laterally above the incision line. A single layer closure of capsule and retinaculum is performed with #2-0 chromic suture with the knee flexed 30 degrees for the first several sutures, then to 60 degrees with the second set of sutures, and finally, to 90 degrees for the remaining closure sutures. Subcutaneous tissue is closed with #3-0 plain suture, skin is re-approximated in a tension-free fashion with #3-0 nylon suture. Hemovac drains are hooked to suction and a Robert-Jones compression dressing is applied. The leg is elevated and the patient is taken to the recovery room where ice packs are placed about the knee.

It will be understood by those skilled in the art that many modifications and variations of the present invention may be made without departing from the spirit and the scope thereof.

What is claimed is:

1. An improved prosthetic joint with congruent bearing surface engagement and for providing only two degrees of freedom of rotational movement between a first bone and a second bone, said first bone having an axis; and said prosthetic joint periodically being under compressive load transmitted thereto by said bones; which comprises:
    a first component for being secured to said first bone and providing a first bearing surface;
    a second component for being secured to said second bone and providing a second bearing surface which is a smooth, continuous surface formed by a series of segments of surfaces of revolution the respective shapes of which are generated by rotating a common generating curve around a plurality of generating axes at respective pairs of major generating radii and through respective angles of rotation, one of said segments of surfaces of revolution being the primary load bearing segment;
    an intermediate bearing component intermediate said first and second components and provided with:
        (i) a third bearing surface substantially congruent with said first bearing surface and for substantially congruent area rotational engagement therewith to permit relative rotational movement of said first component with respect to said intermediate bearing and said second components about a second predetermined axis not parallel to said first predetermined axis and thereby providing only one of said two degrees of freedom of rotational movement, and where said second predetermined axis is substantially parallel to said axis of the first bone,
    and
        (ii) a fourth bearing surface defined by rotating said common generating curve through a predetermined angle about a predetermined generating axis at the same pair of major generating radii at which said common generating curve is rotated to define said primary load bearing segment, said fourth bearing surface for substantially congruent sliding engagement with said primary load bearing segment and for engaging other of the remaining segments of surfaces of revolution in substantial line contact sliding engagement to permit relative rotational movement of said first and intermediate bearing components with respect to said second component about said first predetermined axis and thereby providing said second degree of freedom of rotational movement and inhibiting rotation of the intermediate bearing component relative to said second component about any axis but said predetermined first axis upon said bearing surfaces being in engagement due to said compressive loads being transmitted to said prosthetic joint.

2. An improved prosthetic joint according to claim 1 wherein said series of segments of surfaces of revolution are a series of tangent segments of surfaces of revolution.

3. An improved prosthetic joint according to claim 1 or 2 wherein said prosthetic joint is a knee joint for providing the tibial-femoral articulation and wherein said first component is a tibial platform component for being secured to the proximal end of the tibial; wherein said second component is a femoral component for being secured to the distal end of the femur; and wherein said intermediate component is an intermediate tibial bearing component.

4. An endoprosthesis having congruent engagement between engaged bearing surfaces, comprising:
    A. A first prosthesis for being secured to a first bone and providing a first bearing surface the shape of which is a smooth, continuous surface formed by a series of segments of surfaces of revolution the respective shapes of which are generated by rotating a common generating curve around a plurality of predetermined generating axes at predetermined plurality of predetermined generating axes at predetermined respective angles of rotation, one of said series of segments of surfaces of revolution being the primary load bearing segment;
    B. a second prosthesis including:
        (i) a platform or fixturing component for being secured to a second bone and providing a second bearing surface;
        (ii) an intermediate bearing component for being positioned intermediate said platform or fixturing component and said first prosthesis, said intermediate bearing component being received and supported rotatably by said platform or fixturing component in substantially congruent area rotational engagement to permit rotational movement between the first and second bones and further provided with a third bearing surface for substantially congruent area sliding engagement with said first bearing surface of said first prosthesis to permit rotational movement of one bone around the other bone, said third bearing surface being a primary load bearing surface the shape of which is generated by rotating said common generating curve through a predetermined angle about a predetermined generating axis at the same pair of major generating radii at which said common generating curve is rotated to generate said primary load bearing segment whereby said third bearing surface congruently matches said primary load bearing segment of said first prosthesis.

5. An improved knee prosthetic joint with congruent bearing surface engagement and for providing only two degrees of freedom of rotational movement between a patella and a femur, said patella having an axis and wherein said prosthetic knee joint is periodically under compressive loads transmitted thereto by such bones, which comprises:

a patella fixturing component for being secured to at least a remnant of the patella and providing a first bearing surface;

a femoral component for being secured to the distal end of the femur and providing a second bearing surface which is a smooth, continous surface formed by a series of segments of surfaces of revolution the respective shapes of which are generated by rotating a common generating curve around a plurality of first predetermined generating axes at predetermined respective pairs of major generating radii and through predetermined respective angles of rotation; one of said series of segments of surfaces of revolution being the femoral primary load bearing segment;

a patella intermediate bearing component intermediate said patella fixturing component and said femoral component and provided with:

(i) a third bearing surface substantially congruent with said first bearing surface and for substantially congruent area rotational engagement therewith to permit relative rotational movement of said patella fixturing component with respect to said patella intermediate bearing component and said femoral component about a second predetermined axis not parallel to said first predetermined generating axes and thereby providing the first degree of said only two degrees of freedom of rotational movement and wherein said second predetermined axis is substantially parallel to the axis of the patella, and (ii) a fourth bearing surface, comprised of less than half a surface of revolution, substantially congruent with said second bearing surface and for substantially congruent sliding engagement therewith to permit relative rotational movement of said patella fixturing component and said patella intermediate bearing component with respect to said femoral component about said first predetermined generating axes and thereby providing the second degree of said only two degrees of freedom of rotational movement and inhibiting rotation of said patella intermediate bearing component relative to said femoral component about any axes but said first predetermined generating axes upon said bearing surfaces being in engagement due to said compressive loads being transmitted to said knee prosthetic joint.

6. An improved knee prosthetic joint for allowing all normal degrees of freedom of joint rotational movement between the tibia and femur and providing congruent bearing surface engagement during predetermined portions of all such rotational movement, but upon compressive load being applied to said joint, said joint providing only two degrees of freedom of rotational movement between said tibia and femur, said tibia having a long axis, which comprises:

a tibial platform component for being secured to the proximal end of the tibia and providing a first bearing surface;

a femoral component for being secured to the distal end of the femur and providing a second bearing surface which is a smooth, continuous surface formed by a series of segments of surfaces of revolution the respective shapes of which are generated by rotating a common generating curve around a plurality of generating axes at respective pairs of major generating radii and through respective angles of rotation, one of said segments of surfaces of revolution being the primary load bearing segment;

an intermediate tibial bearing component intermediate said tibial platform component and said femoral component and provided with:

(i) a third bearing surface substantially congruent with said first bearing surface and for substantially congruent area rotational engagement therewith to permit relative rotational movement of said tibial platform component with respect to said intermediate tibial bearing component and said femoral component about a second predetermined axis not parallel to said plurality of generating axes and thereby providing the first degree of said only two degrees of freedom of rotational movement, and where said second predetermined axis is generally parallel to the long axis of the tibia, and (ii) a fourth bearing surface defined by rotating said common generating curve through a predetermined angle about a predetermined generating axis at the same pair of major generating radii at which said common generating curve is rotated to define said primary load bearing segment whereby said fourth bearing surfce congruently matches said primary load bearing segment for substantially congruent sliding engagement therewith during predetermined portions of such engagement to permit all other of said normal degrees of freedom of joint rotational movement in the absence of said sufficient compressive load, but upon said compressive load, being applied to said knee prosthetic joint, said fourth and second bearing surfaces providing only said second degree of said only two degrees of freedom of rotational movement.

7. An improved endoprosthesis for providing the articular surfaces between a first bone and a second bone, comprising:

a first endoprosthesis component for being secured to said first bone and providing a first articular surface;

a second endoprosthesis component for being secured to said second bone and for providing a second articular surface for articulating with said first articular surface;

said first articular surface being a smooth continuous surface formed by a series of segments of tangent surfaces of revolution the respective shapes of which are generated by rotating a common generating curve around a plurality of predetermined generating axes at predetermined respective pairs of major generating radii and through predetermined respective angles of rotation; and said second articular surface being generated by rotating said common generating curve through a predetermined angle about a predetermined generating axis at the same pair of major generating radii at which said common generating curve is rotated to generate one segment of said first articular surface whereby upon said second articular surface articulating with said first articular surface, said second articular surface articulating with said one segment of said first articular surface in substantially area sliding contact and articulating with said remaining segments of said first articular surface in substantially line sliding contact.

8. A knee endoprosthesis having congruent engagement between engaged bearing surfaces comprising:
   A. A femoral prosthesis for being secured to the distal end of the femur and providing a femoral bearing surface the shape of which is a smooth, continuous surface formed by a series of segments of tangent surfaces of revolution the respective shapes of which are generated by rotating a common generating curve around a plurality of predetermined generating axes at predetermined respective pairs of major generating radii and through predetermined respective angles of rotation, one of said series of segments of surfaces of revolution being the femoral primary load bearing segment; and
   B. A patella prosthesis including a patella load bearing surface for engaging said femoral bearing surface in substantially congruent sliding engagement to permit rotational movement of said patella round the distal end of the femur, said patella bearing surface including a patella primary load bearing surface segment the shape of which is defined by rotating said common generating curve through a pedetermined angle about a predetermined generating axis at the same pair of major generating radii at which said common generating curve is rotated to define said femoral primary load bearing segment whereby said patella primary load bearing segment congruently matches said femoral primary load bearing segment.

9. A knee endoprosthesis having substantially congruent area sliding engagement between engaged bearing surfaces upon said endoprosthesis being under heavy joint compressive loads, comprising:
   A. A femoral prosthesis for being secured to the distal end of the femur and providing a femoral bearing surface the shape of which is smooth, continuous surface formed by a series of segments of tangent surfaces of revolution the respective shapes of which are generated by rotating a common generating curve around a plurality of predetermined generating axes at predetermined respective pairs of major generating radii and through predetermined respective angles of rotation, one of said series of segments of surfaces of revolution being the femoral primary load bearing segment; and
   B. A tibial prosthesis including a tibial primary load bearing surface for engaging said femoral load bearing surface in sliding engagement to permit rotational movement of the tibia around the distal end of the femur and said tibial primary load bearing surface engaging said femoral primary load bearing segment in sliding engagement upon said endoprosthesis being under said compressive loads, the shape of said tibial primary bearing surface being defined by rotating said common generating curve though a predetermined angle about a predetermined generating axis at the same pair of major generating radii at which said common generating curve is rotated to define said femoral primary load bearing segment whereby said tibial primary bearing surface substantially congruently matches said femoral primary load bearing segment and engages said femoral primary load bearing segment in substantially congruent area sliding contact upon said endoprosthesis being under said compressive loads.

10. A knee endoprosthesis having congruent engagement between engaged bearing surfaces comprising:
   A. A femoral prosthesis for being secured to the distal end of the femur and providing a femoral bearing surface the shape of which is a smooth, continuous surface formed by a series of segments of surfaces of revolution the respective shapes of which are generated by rotating a common generating curve around a plurality of predetermined generating axes at predetermined respective pairs of major generating radii and through predetermined respective angles of rotation, one of said series of segments of surfaces of revolution being the femoral primary load bearing segment;
   B. A patella prosthesis including a patella load bearing surface for engaging said femoral bearing surface in substantially congruent sliding engagement to permit rotational movement of said patella round the distal end of the femur, said patella bearing surface including a patella primary load bearing surface segment the shape of which is defined by rotating said common generating curve through a predetermined angle about a predetermined generating axis at the same pair of major generating radii at which said common generating curve is rotated to define said femoral primary load bearing segment whereby said patella primary load bearing segment congruently matches said femoral primary load bearing segment;
   C. A tibial prosthesis including a tibial primary load bearing surface for engaging said femoral load bearing surface in substantially congruent sliding engagement to permit rotational movement of the tibia around the distal end of the femur, the shape of said tibial primary bearing surface being defined by rotating said common generating curve through a predetermined angle about a predetermined generating axis at the same pair of major generating radii at which said common generating curve is rotated to define said femoral primary load bearing segment whereby said tibial primary bearing surface congruently matches said femoral primary load bearing segment.

11. A knee endoprosthesis having congruent engagement between engaged bearing surfaces, comprising:
   A. A femoral prosthesis for being secured to the distal end of the femur and providing a first bearing surface the shape of which is a smooth, continuous surface formed by a series of segments of surfaces of revolution the respective shapes of which are generated by rotating a common generating curve around a plurality of predetermined generating axes at predetermined respective angles of rotation, one of said series of segments of surfaces of revolution being the primary load bearing segment; and
   B. A patella prosthesis including:

(i) a patella fixturing component for being secured to at least a remnant of the patella and providing a second bearing surface;

(ii) an intermediate patella bearing component for being positioned intermediate said patella fixturing component and said femoral prosthesis, said intermediate patella bearing component being received and supported rotatably by said patella fixturing component and providing a third bearing surface for rotatably engaging said second bearing surface provided on said patella fixturing component in substantially congruent area rotational engagement to permit rotational movement between the patella and the distal end of the femur and further provided with a fourth bearing surface provided on said patella prosthesis in substantially congruent sliding area engagement to permit rotational movement of said patella around the distal end of said femur, said fourth bearing surface including a primary load bearing surface segment the shape of which is generated by rotating said common generating curve through a predetermined angle about a predetermined generating axis at the same pair of major generating radii at which said common generating curve is rotated to generate said primary load bearing segment whereby said primary load bearing surface segment congruently matches said primary load bearing segment of said femoral prosthesis.

12. A knee endoprosthesis having congruent and incongruent sliding engagement between engaged bearing surfaces, comprising:

A. A femoral prosthesis for being secured to the distal end of the femur and providing a first bearing surface the shape of which is a smooth, continuous surface formed by a series of segments of surfaces of revolution the respective shapes of which are generated by rotating a common generating curve around a plurality of predetermined generating axes at predetermined respective angles of rotation, one of said series of segments of surfaces of revolution being the primary load bearing segment;

B. A tibial prosthesis including:

(i) a tibial platform component for being secured to the proximal end of a tibia and providing a second bearing surface;

(ii) an intermediate tibial bearing component for being positioned intermediate said tibial platform component and said femoral prosthesis, said intermediate tibial bearing component being received and supported rotatably by said tibial platform component in substantially congruent area rotational engagement to permit rotational movement between the tibia and the femur and further provided with a third bearing surface generated by rotating said common generating curve through a predetermined angle about a predetermined generating axis at the same pair of major generating radii at which said common generating curve is rotated to generate said primary load bearing segment, said third bearing surface for engaging said primary load bearing segment, in substantially congruent area sliding engagement and for engaging other of the remaining segments of said series of segments of surfaces of revolution of said first bearing surface in substantially line contact sliding engagement to permit rotational movement of the tibia around the distal end of the femur.

13. A knee endoprosthesis having congruent engagement between engaged bearing surfaces, comprising:

A. A femoral prosthesis for being secured to the distal end of the femur and providing a first bearing surface the shape of which is a smooth, continuous surface formed by a series of segments of surfaces of revolution the respective shapes of which are generated by rotating a common generating curve around a plurality of predetermined generating axes at predetermined respective angles of rotation, one of said series of segments of surfaces of revolution being the primary load bearing segment;

B. A patella prosthesis including:

(i) a patella fixturing component for being secured to at least a remnant of the patella and providing a second bearing surface;

(ii) an intermediate patella bearing component for being positioned intermediate said patella fixturing component and said femoral prosthesis, said intermediate patella bearing component being received and supported rotatably by said patella fixturing component and providing a third bearing surface for rotatably engaging said second bearing surface provided on said patella fixturing component in substantially congruent area rotational engagement to permit rotational movement between the patella and the distal end of the femur and further provided with a fourth bearing surface provided on said patella prosthesis in substantially congruent sliding area engagement to permit rotational movement of said patella around the distal end of said femur, said fourth bearing surface including a primary load bearing surface segment the shape of which is generated by rotating said common generating curve through a predetermined angle about a predetermined generating axis at the same pair of major generating radii at which said common generating curve is rotated to generate said primary load bearing segment whereby said primary load bearing surface segment congruently matches said primary load bearing segment of said femoral prosthesis;

C. A tibial prosthesis including:

(i) a tibial platform component for being secured to the proximal end of said tibia and providing a fifth bearing surface;

(ii) an intermediate tibial bearing component for being positioned intermediate said tibial platform component and said femoral prosthesis, said intermediate tibial bearing component being received and supported rotatably by said tibial platform component in substantially congruent area rotational engagement to permit rotational movement between the tibial and the femur and further provided with a sixth bearing surface for substantially congruent area sliding engagement with said firtst bearing surface of said femoral prosthesis to permit rotational movement of the tibia around the distal end of the femur, said sixth bearing surface being a primary load bearing surface the shape of which is generated by rotating said common generating curve through a predetermined angle about a predetermined generating axis at the same pair of major generating radii at which said common generating curve is rotated to generate said primary load bearing segment whereby said sixth bearing surface congruently matches said primary load bearing segment of said femoral prosthesis.

14. A knee endoprosthesis according to any of claims 5-12 or 13 wherein said common generating curve is a smooth, continuous plane curve the shape of which is defined by (i) first and second predetermined arcs struck, respectively, by first and second predetermined radii from respective predetermined centers separated by a predetermined distance; (ii) two predetermined lines respectively tangent to said first and second predetermined arcs and at respective predetermined angles with respect to a predetermined line tangent to said first and second predetermined arcs; and (iii) a third predetermined arc struck by a third predetermined radius from a third predetermined center and wherein said third predetermined arc is also tangent to said first and second predetermined tangent lines.

15. A knee endoprosthesis, comprising:
   A. A femoral prosthesis for being secured to the distal end of the femur and providing a femoral bearing surface the shape of which is generated by rotating a common generating curve around a first predetermined generating axis at a first predetermined respective pair of major generating radii and through a first predetermined respective angle of rotation;
   B. A patella prosthesis including a patella load bearing surface for engaging said femoral bearing surface in sliding engagement to permit rotational movement of said patella around the distal end of the femur, said patella bearing surface generated by rotating said common generating curve around a second predetermined generating axis at a second predetermined pair of major generating radii and through a second predetermined angle of rotation;
   C. A tibial prosthesis including a tibial load bearing surface for engaging said femoral load bearing surface in sliding engagement to permit rotational movement of the tibia around the distal end of the femur, said tibial load bearing surface generated by rotating said common generating curve around a third predetermined generating axis at a third pair of major generating radii and through a third predetermined angle of rotation; and
   D. upon said patella load bearing surface and said tibial load bearing surface engaging said femoral load bearing surface in said sliding engagement, said patella and said tibial load bearing surfaces engaging said femoral load bearing surface in at least line contact thereby reducing wear of said load bearing surfaces due to said sliding engagement.

16. An endoprosthesis, comprising:
   A. A first prosthetic component for being secured to a first bone and providing a first bearing surface the shape of which is generated by rotating a common generating curve around the first predetermined generating axis at a first predetermined respective pair of major generating radii and through a first predetermined respective angle of rotation;
   B. A second prosthetic component for being secured to a second bone and providing a second load bearing surface for engaging said first load bearing surface in sliding engagement to permit movement of said first bone with respect to said second bone, said second load bearing surface generated by rotating said common generating curve around a second predetermined generating axis at a second predetermined pair of major generating radii and through a second predetermined angle of rotation;
   C. A third prosthetic component for being secured to a third bone providing a third load bearing surface for engaging said first load bearing surface in sliding engagement to permit movement of said third bone with respect to said first bone, said third load bearing surface generated by rotating said common generating curve around a third predetermined generating axis at a third pair of major generating radii and through a third predetermined angle of rotation; and
   D. Upon said second and third load bearing surfaces engaging said first load bearing surface in said sliding engagement, said second and third load bearing surfaces engaging said first load bearing surface in at least line contact thereby reducing wear of said load bearing surfaces due to said sliding engagement.

17. An improved prosthetic joint for providing movement between a first bone and a second bone, said prosthetic joint periodically being under compressive load transmitted thereto by said bones, which comprises:
   a first component for being secured to said first bone and providing a first bearing surface;
   a second component for being secured to said second bone and providing a second bearing surface;
   an intermediate bearing component intermediate said first and second components provided with:
      (i) a third bearing surface substantially congruent with said first bearing surface and for substantially congruent sliding engagement therewith during joint articulation.
      (ii) a fourth bearing surface incongruent with predetermined portions of said second bearing surface and congruent with predetermined other portions of said second bearing surface, said fourth bearing surface for sliding engagement with said second bearing surface to permit movement of said first and intermediate bearing components with respect to said second bone.

18. A knee endoprothesis, comprising:
   A. A femoral prosthesis for being secured to the distal end of the femur and providing a femoral bearing surface the shape of which is a smooth, continuous surface formed by at least first, second and third segments of surfaces of revolution the respective shapes of which are generated by rotating a common generating curve around at least three respective predetermined generating axes at three predetermined respective pairs of major generating radii and through three predetermined respective angles of rotation, said second segment of a surface of revolution being the femoral primary load bearing segment;
   B. (i) A patella prosthesis for being secured to at least a remnant of the patella and providing a patella load bearing surface the shape of which is defined by rotating said common generating curve through a predetermined angle around a predetermined generating axis at the same pair of major generating radii at which said common generating curve is rotated to define said femoral primary load bearing surface,
      (ii) upon said patella rotating around the distal end of said femur, said patella load bearing surface engaging said femoral bearing surface in sliding engagement with said patella load bearing surface engaging said first segment of a surface of revolution forming said femoral bearing surface in at least line contact and engaging said second segment of surface of revolution forming said femoral bearing surface in area contact; and C. (i) a tibial prosthesis for being secured to the proximal end of the tibia and providing a tibial load bearing surface the shape of which is defined by rotating said common generating curve through a predetermined angle about a predetermined major axis at the same pair of major generating radii at which said common generating curve is rotated to define said femoral primary load bearing surface;

(ii) upon said tibia rotating around the distal end of said femur, said tibial load bearing surface engaging said femoral bearing surface in sliding engagement with the tibial load bearing surface engaging said second segment of surface of revolution forming said femoral bearing surface in area contact and engaging said third segment of surface of revolution forming said femoral bearing surface in at least line contact.

* * * * *